United States Patent
Hu et al.

(10) Patent No.: US 11,433,108 B2
(45) Date of Patent: Sep. 6, 2022

(54) ANTI-CANCER ONCOLYTIC VIRUS COMBINATION THERAPIES AND ELITE RESPONDER SELECTION PLATFORMS

(71) Applicants: Minjie Hu, Foster City, CA (US); Yu Li, Johns Creek, GA (US); Xiaoling Liu, Pearland, TX (US); Rebecca Hu, Foster City, CA (US)

(72) Inventors: Minjie Hu, Foster City, CA (US); Yu Li, Johns Creek, GA (US); Xiaoling Liu, Pearland, TX (US); Rebecca Hu, Foster City, CA (US)

(73) Assignee: SUZHOU PRAJNA BIOTECH CO., LTD., Suzhou (CN)

( * ) Notice: Subject to any disclaimer, the term of this patent is extended or adjusted under 35 U.S.C. 154(b) by 259 days.

(21) Appl. No.: 15/744,295

(22) PCT Filed: Mar. 28, 2017

(86) PCT No.: PCT/US2017/024471
§ 371 (c)(1),
(2) Date: Jan. 12, 2018

(87) PCT Pub. No.: WO2017/172713
PCT Pub. Date: Oct. 5, 2017

(65) Prior Publication Data
US 2019/0000899 A1    Jan. 3, 2019

Related U.S. Application Data

(60) Provisional application No. 62/390,395, filed on Mar. 28, 2016.

(51) Int. Cl.
*A61K 35/768* (2015.01)
*A61K 39/39* (2006.01)
(Continued)

(52) U.S. Cl.
CPC .......... *A61K 35/768* (2013.01); *A61K 35/741* (2013.01); *A61K 35/745* (2013.01);
(Continued)

(58) Field of Classification Search
CPC .... A61K 35/768; A61K 39/39; A61K 35/745; A61K 2039/55594; A61P 35/00
See application file for complete search history.

(56) References Cited

U.S. PATENT DOCUMENTS 7,763,420 B2    7/2010    Stritzker et al.
7,820,184 B2    10/2010   Stritzker et al.
(Continued)

FOREIGN PATENT DOCUMENTS

WO    WO-2012122649 A1 *    9/2012    .............. A61P 35/00

OTHER PUBLICATIONS

Kenneth J. Ellis, Reference Man and Woman More Fully Characterized, Variations on the Basis of Body Size, Age, Sex, and Race, 1990, Biological Trace Element Research, Editor: G. N. Schrauzer, The Humana Press Inc, pp. 385-400 (Year: 1990).*
(Continued)

*Primary Examiner* — David W Berke-Schlessel
*Assistant Examiner* — Trent R Clarke
(74) *Attorney, Agent, or Firm* — Finnegan, Henderson, Farabow, Garrett & Dunner LLP

(57) ABSTRACT

Therapeutic methods for administering gut microbiota and oncolytic viruses to a subject are provided. The gut microbiota serve to pre-condition, the subject's immune system to antitumor responses and augments anticancer activity of the oncolytic vims. Combinations of the gut. microbiota and viruses and uses thereof for treating and preventing cancer are provided. The present disclosure also provides methods
(Continued)

for building elite responder selection platforms through hierarchical clustering analysis of genomic profiles for human gut microbiome.

9 Claims, 13 Drawing Sheets

Specification includes a Sequence Listing.

(51) Int. Cl.
| | |
|---|---|
| *A61K 35/745* | (2015.01) |
| *A61P 35/00* | (2006.01) |
| *A61K 35/741* | (2015.01) |
| *A61K 45/06* | (2006.01) |
| *C12N 7/00* | (2006.01) |
| *A61K 39/00* | (2006.01) |

(52) U.S. Cl.
CPC .............. *A61K 39/39* (2013.01); *A61K 45/06* (2013.01); *A61P 35/00* (2018.01); *C12N 7/00* (2013.01); *A61K 2039/55594* (2013.01); *C12N 2710/24021* (2013.01); *C12N 2710/24032* (2013.01); *C12N 2710/24121* (2013.01); *C12N 2710/24132* (2013.01)

(56) References Cited

U.S. PATENT DOCUMENTS

| | | | |
|---|---|---|---|
| 8,859,256 | B2 | 10/2014 | Szalay et al. |
| 9,492,534 | B2 | 11/2016 | Szalay et al. |
| 2012/0014990 | A1 | 1/2012 | Lichty et al. |
| 2013/0130292 | A1 | 5/2013 | Szalay et al. |
| 2013/0280170 | A1 | 10/2013 | Szalay et al. |
| 2014/0271549 | A1 | 9/2014 | Szalay |
| 2015/0024403 | A1 | 1/2015 | Szalay et al. |
| 2016/0058591 | A1 | 3/2016 | Bangera et al. |

OTHER PUBLICATIONS

Alexander A. Bachmanov, Danielle R. Reed, Gary K. Beauchamp, and Michael G. Tordoff, Food Intake, Water Intake, and Drinking Spout Side Preference of 28 Mouse Strains, 2002, Behav. Genet., vol. 32, No. 6, pp. 435-443 (Year: 2002).*
Cronin et al., "Bacterial-Mediated Knockdown of Tumor Resistance to an Oncolytic Virus Enhances Therapy", Molecular Therapy, 22(6):1188-1197 (2014).
Gui et al., "Well-balanced commensal microbiota contributes to anti-cancer response in a lung cancer mouse model", Genetics and Molecular Res. GMR, 14(2):5642-5651 (2015).
Li et al., "Probiotics modulated gut microbiota suppresses hepatocellular carcinoma growth in mice", Proc. Nat. Acad. Sci. 113(9):E1306-E1315 (2016).
Supplementary European Search Report for EP 17 77 6429 dated Oct. 9, 2019.
Breitbach, C.J. et al., "Intravenous Delivery of a Multi-Mechanistic Cancer-Targeted Oncolyutic Poxvirus in Humans," Nature Letter, 477: 99-104 (2011).
Culligan, E.P. et al., "Metagenomics and Novel Gene Discovery," Virulence, 5:399-412 (2014).
Burke, J. et al., "Oncolytic Viruses: Perspectives on Clinical Development," Curr. Opinion Virol., 13:55-60 (2015).
Delhon et al., "Genomes of the Parapoxyviruses Orf Virus and Bovine Papular Stomatitis Virus." J. Virol. 78(1):168-177 (2004).
De Vries, C.R. et al., "Oncolytic Viruses: Focusing on the Tumor Microenvironment," Can. Gene Ther., 22:169-171 (2015).
Dzutsev et al., "The Role of the Microbiota in Inflammation, Carcinogenesis, and Cancer Therapy." Eur. J. Immunol. 45:17-31 (2015).
Etzold, S. et al., "Structural Basis for Adaptation of Lactobacilli to Gastrointestinal Mucus," Environ. Microbiol., 16:888-903 (2014).
Fransen, F. et al., "BALB/c And C57BL/6 Mice Differ in Polyreactive IgA Abundance, Which Impacts the Generation of Antigen-Specific IgA and Microbiota Diversity," Immunity, 43:527-540 (2015).
Gajewski, T.F. et al., "Gene Signature in Melanoma Associated With Clinical Activity," The Cancer Journal, 16:1-16(2010).
Hill, C. et al., "The International Scientific Association for Probiotics and Prebiotics Consensus Statement on the Scope and Appropriate Use of the Term Probiotic," Nature, 11:508-514 (2014).
International Search Report and Written Opinion PCT/US2017/02441 dated Jul. 27, 2017.
Ji, R.R. et al., "An Immune-Active Tumor Microenviroment Favors Clinical Response to Ipilimumab," Cancer Immunol. Immunother., 61:1019-1031 (2012).
Kaufman, H.L. et al., "Oncolytic Viruses: A New Class of Immunotherapy Drugs," Cancer Immunotherapy, 14:642-662 (2015).
Lida, N. et al., "Commensal Bacteria Control Cancer Response to Therapy by Modulating the Tumor Microenvironment," Science, 342:967-970 (2013).
Ng, S.C. et al., "Mechanisms of Action of Probiotics: Recent Advances," Inflamm. Bowel Dis., 15:300-310 (2009).
Pikor, L.A. et al., "Oncolytic Viruses: Exploiting Cancer's Deal With the Devil," Trends in Cancer, 1:266-277 (2015).
Prieto, J. et al., "Immunological Landscape and Immunotherapy of Hepatocellular Carcinoma," Nature Reviews, 1-20 (2015).
Rubin, K., "Understanding Immune Checkpoint Inhibitors for Effective Patient Care," Clin. J. Oncol. Nursing, 19:709-717 (2015).
Shlien, A. et al., "Combined Hereditary and Somatic Mutations of Replication Error Repair Genes Result in Rapid Onset of Ultra-Hypemiutated Cancers," Nature Genetics, 1-8 (2015).
Turnbaugh, P.J. et al., "A Core Gut Microbiome in Obese and Lean Twins," Nature, 457:480-484 (2009).
Turnbull, S. et al., "Evidence For Oncolytic Virotherapy: Where Have We Got to and Where are We Going," Viruses, 7:6291-6312, (2015).
Viaud et al., "The Intestinal Micriobiota Modulates the Anticancer Immune Effects of Cyclophosphamide." Science, 342:971-976 (2013).

* cited by examiner

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
cgggggtgct gcccactttc atg                                            23

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gcttgttggt gaggtaacgg ct                                             22

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gtgccagcmg ccgcggtaa                                                 19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggactachvg ggtwtctaat                                                20

<210> SEQ ID NO 5
<211> LENGTH: 17
<212> TYPE: DNA
<213> ORGANISM: Artificial Sequence
<220> FEATURE:
<223> OTHER INFORMATION: Primer
```

```
<400> SEQUENCE: 5 cctayggqrb gcascag                                                  17

<210> SEQ ID NO 6
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (8)..(9)
<223> OTHER INFORMATION: n is a, c, g, or t

<400> SEQUENCE: 6
ggactacnng ggtatctaat                                               20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gtgccagcmg ccgcggtaa                                                19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ccgtcaattc ctttgagttt                                               20
```

ANTI-CANCER ONCOLYTIC VIRUS COMBINATION THERAPIES AND ELITE RESPONDER SELECTION PLATFORMS

RELATED APPLICATIONS

This application is a national stage filing under 35 U.S.C. § 371 of International Application No. PCT/US2017/024471, filed on Mar. 28, 2017. which claims priority under 35 U.S.C § 119(e) to U.S. Provisional Application Ser. No. 62/390,395 filed Mar. 28, 2016. The contents of these applications are each herein incorporated fully by reference. The sequence listing "15744.295_Sequence_listing.txt" created Jan. 12, 2018, in ASCII format and having a size of 1.74 kilobytes is herein incorporated fully by reference.

FIELD

The present disclosure provides methods for administering to a subject gut microbiota and oncolytic viruses. Combinations of the viruses and gut microbiota and uses thereof for treating and preventing cancer are also provided.

BACKGROUND

Cancer consists of a group of diseases marked by uncontrolled growth of malignant cells. There are over one hundred cancers that affect a large segment of the human population and account for about 13% of all fatalities. Cancer was responsible for over 8.2 million deaths worldwide in 2012, and this number is predicted to jump to 13 million by 2030. The number of new cancer cases diagnosed in 2012 worldwide was 14.1 million, and 58% of new cancer cases are found in developed countries like the US. Among children ages 0 to 14, an estimated 163,300 new cases were diagnosed in 2012, of which about 80,000 resulted in death (WHO, World Health Report 2014; National Center for Health Statistics, 2014; ACS, Global Cancer Facts & Figures, 2015).

Current existing cancer therapies include radiation, surgery, chemotherapy, targeted therapy, immune therapy, oncolytic-virus (OV)-based therapies, or a combination of the above (ACS, Global Cancer Facts & Figures, 2015). Patient response to therapy depends on the specific cancer type, the disease stage, and the particular therapy being used, which may determine the patient's total survival time (National Center for Health Statistics, 2014). Unfortunately, only a small minority of patients can be completely cured with one of the above therapeutic treatments (WHO, World Health Report, 2014). Cancer metastasis, the translocation of the primary cancer from its origin into other parts of the body, is often associated with the late stages of a cancer and results in the most cancer deaths (National Comprehensive Cancer Network, What is Metastasized Cancer?, 2016). Cancer is highly linked to old age (Coleman & Rubinas, Elsevier Academic Press, p. 66, 2009), which highlights the urgency for developing an effective therapy due to our aging population.

Recent technical advancements in DNA sequencing and bioinformatics have made it possible to carefully analyze genomic aberration profiles of samples from different patients. These analyses have uncovered the extensive inter-patient and intra-tumor heterogeneity and ongoing clonal adaptation in human tumors, which contain spatially and temporally separated and role-changing subclones with different driver and passenger mutation landscapes (Lipinski, Trends Cancer 2(1): 49-63, 2016). This discovery indicates that cancer is a randomized and evolving process, with its mutation load changing in number and composition clone-to-clone or even cell-to-cell within a given tumor (Shlien et al., Nat. Genet. 47, 257-262, 2015). This may affect the varying responses to therapies for individual cancers, and explains the development process of drug resistance and certain clinical failures. This phenomenon certainly questions the feasibility of a widely used therapy strategy, which treats dynamically evolving tumor 'organisms' through precise molecular targeting, and begs the need for a more systemic approach. "Precise therapies" as those with defined molecular targets, which include most chemotherapies, humoral immunotherapy using monoclonal antibodies, and the recent advanced chimeric antigen receptor T (Car T) cell therapy. On the other hand, "systematic treatments" are those whose efficacy relies on the systemic activation of the host immune system, including immune cell therapy (CIK, NK, TIL et al.), checkpoint inhibitor therapy, and OV therapy. Responses from "precise therapies" tend to be relatively transient, while "systematic treatments" usually give good levels of long-term responses, which could translate into long-term survival.

Checkpoint inhibitor therapy acts by modulating the host systemic immune response (La-Beck, Pharmacotherapy 35(10): 963-76, 2015; Rubin, Clin J Oncol Nurs. 19(6):709-17, 2015; Sharma & Allison, Science 348(6230): 56-61, 2015). The clinical efficacy of checkpoint inhibitor therapy in regulating either the key T cell priming player—the cytotoxic T lymphocyte antigen-4 (CTLA-4)—or the major T cell function suppressors—the programmed cell death protein-1 (PD-1) and its ligand PDL-1-led to FDA approval of these antibodies for treatment of metastatic melanoma (MM) and other solid tumors (Hodi et al., N. Engl. J. Med. 363, 711-23, 2010; Prieto et al., Nat. Rev. Gastroenterol. Hepatol. 12, 681-700, 2015). However, only a subset of patients respond to the antibody treatments, and the efficacy with any single therapy remains limited (Chodon et al., Immunol Invest. 44(8): 817-36, 2015). In addition, only a 50% response rate (which translates to a 22% complete response rate) has been reported, even in combination with the oncolytic virus T-Vec (Puzanov et al., J. Clin. Oncol. 33, S9063, 2015). On the other hand, patients with ongoing intratumoral T cell response before therapy usually respond more frequently to the antibody treatment (Ji, Cancer Immunol Immunother. 61(7): 1019-31, 2012; Gajewski, Cancer J. 16(4): 399-403, 2010; Tumeh, Nature 515(7528): 568-71, 2014). In addition, mice fed with antibodies showed a significant decease in the activation of both CD4$^+$ T effector cells and CD8$^+$ tumor infiltrating lymphocytes (TIL), which play a critical role in the adaptive immune response during antibody-initiated tumor killing. There remains a need in the art to improve upon this therapy by enhancing the immune response in the intratumoral space. Therefore, among the objects herein, it is an object to provide therapeutic methods that pre-condition a subject's immune system to antitumor responses and augment the anticancer activity of existing anti-cancer "systematic treatments."

Oncolytic viruses (OV) are therapeutically used microbes (either naturally occurring or genetically-engineered) that preferentially infect and replicate in cancer cells in order to eliminate malignant tumors while avoiding toxicity (Seymour & Fisher, Br. J. Cancer 114(4): 357-61, 2016; Kaufman et al., Nat. Rev. Drug Discov. 14(9): 642-62, 2015; Turnbull et al., Viruses 7(12): 6291-312, 2015; Larissa et al., Trends Cancer 1(4): 266-77, 2015). Oncolytic viruses target tumor cells precisely because the same genetic alterations that allow malignant tumor cells to proliferate and survive also promote the growth of lytic viruses (Hanahan & Weinberg, *Cell* 144(5): 646-74, 2011; Miest & Cattaneo, *Nat. Rev. Microbiol.* 12(1): 23-34, 2014; Burke et al., *Curr. Opin. Virol.* 13: 55-60, 2015). Additionally, drug-resistant cancer cells and cancer stem cells retain their susceptibility to OV, which are effective in the hypoxic environments characteristic of solid tumors (Shen & Hermiston, *Gene Ther.* 12, 902-10, 2005). Infected OV have the ability to coordinate cancer cell death at a suitable time point within the virus life cycle, which leads to the release of infectious viral particles (Seymour & Fisher, *Br. J. Cancer* 114(4): 357-61, 2016). OV-initiated tumor cell death not only raises the active intratumoral viral dose that infects more tumor cells, but also releases significant amounts of tumor-specific neoantigens that can be presented by intratumoral antigen presenting cells (APCs), such as activated DCs. These cells ignite a host systemic antitumor immune response, a second mechanism of cancer cell killing beyond the direct in situ viral lysis of the tumor (Kaufman et al., *Nat. Rev. Drug Discov.* 14(9): 642-62, 2015). This second mechanism is important for an effective antitumor response, as it will also kill metastatic cancer cells at distant sites previously unseen by the virus as well as intratumoral bystanders localized outside the infected area.

Research into the therapeutic potential of OV started in the 1950s (H-uebner et al., *Cancer* 9, 1211-218, 1956), with clinical trials being held shortly after for a range of cancers (e.g. melanoma, squamous cell carcinoma of the head and neck (SCCHN), pancreatic cancer, ovarian cancer, colorectal cancer, glioma, non-small cell lung cancer (NSCLC), myeloma, breast cancer, prostate cancer, bladder cancer, mesothelioma, hepatocellular carcinoma, and pediatric tumors) with documented therapeutic benefit during the past decade (Kim, *Gene Ther.* 8(2): 89-98, 2001; Kelly & Russell, *Mol. Ther.* 15(4), 651-59, 2007; Eisenstein et al., *Oncolytic Virother.* 3: 83-91, 2014; Miest & Cattaneo, *Nat. Rev. Microbiol.* 12(1): 23-34, 2014; Patil et al., *J. Contemp. Dent. Pract.* 16(8): i-ii, 2015; Burke et al., *Curr. Opin. Virol.* 13: 55-60, 2015; Kaufman et al., *Nat. Rev. Drug Discov.* 14(9): 642-62, 2015). One example is the T-Vec clinical trials, which gave statistically significant improved durable responses and heightened survival rates in patients with unresectable melanoma, expediting FDA approval of the first OV drugs (Andtbacka et al., *J. Clin. Oncol.* 33.25: 2780-00, 2015). While the best OV T-Vec trial showed promising results, there are still a host of problems that need to be addressed. In the 436 Phase III trials, only a 16.3% durable response rate and a 26.4% objective response rate were observed, with only 10.9% of the participants achieving a complete response (Kaufman et al., *Nat. Rev. Drug Discov.* 14(9): 642-62, 2015).

OV has been used in more than 40 clinical trials to treat a spectrum of human malignancies, and one particular therapy has been successfully translated into the first FDA-approved OV drug (Harrington et al., *Expert Rev. Anticancer Ther.* 15(12): 1389-403, 2015). Despite its preliminary success, the efficacy and responsiveness rates across all OV trials remain disappointingly low, especially when factored into the overall survival rate (Buijs et al., *Hum. Vaccin. Immunother.* 11(7): 1573-84, 2015; Burke et al., *Curr. Opin. Virol.* 13: 55-60, 2015; Harrington et al., *Expert Rev. Anticancer Ther.* 15(12): 1389-403, 2015; Kaufman et al., *Nat. Rev. Drug Discov.* 14(9): 642-62, 2015; Patil et al., *J. Contemp. Dent. Pract.* 16(8): i-ii, 2015; Puzanov et al., *J. Clin. Oncol.* 33, S90632015; Turnbull et al., *Viruses* 7(12): 6291-312, 2015). This could be partially derived from the highly suppressive microenvironment within a solid tumor (de Vries et al., *Cancer Gene Ther.* 22(4):169-71, 2015; Church & Galon, *Immunity* 43(4): 631-3, 2015; Clarke, *Immunotherapy* 8(2): 103-6, 2016), which prohibits the OV-initiated adaptive and innate systemic immune responses. It could also be due to the lack of a pre-conditioned anti-tumor immunity by a high percentage of patients, resulting in the low response rates for most systemic anticancer therapies. Therefore, a need exists to develop methods that will increase response rates across all populations.

Commensal gut bacteria have been used as a nutraceutics, such as the probiotic in fermented food containing the *Bifidobacterium* genus within the Gram-positive actinobacteria phylum (Hill et al., *Nat. Rev. Gastroenterol. Hepatol.* 11: 506-14, 2014). It has also been used in routing clinical surgery though fecal microbiota transplantation (FMT) (NICE Interventional Procedure Guidance: 485, 2014). The composition of gut microbiota is regulated by the host's adaptive immune system component secretory immuno-globulins A (sIgAs) (Fransen et al., *Immunity* 43(3): 527-40, 2015). With the aid of several large projects, like the Human Microbiome Project (HMP) (Backhed et al., 2012) and the International Human Microbiome Consortium (IHMC), the understanding of the composition and functions of the human gut microbiota has increased dramatically in the post-metagenomic era (Segata et al., *Genome Biol.* 13:R42, 2012; Segata et al., *Nat. Methods,* 9(8): 811-14, 2012). There are about 100 trillion bacterial cells in the human gut, and they can be categorized into five major phyla, of which approximately 160 species live in the large intestine of any individual (Rajilic-Stojanovic et al., *FEMS Microbiol. Rev.* 38: 996-1047, 2014; Segata et al., *Genome Biol.* 13:R42, 2012).

Unrelated individuals usually do not share similar gut microbiota profiles (Segata et al., *Genome Biol.* 13:R42, 2012; Segata et al., *Nat. Methods,* 9(8): 811-14, 2012) and these differences could reflect differences in immune responses. An individual's gut microbiome can be analyzed by two methodological approaches: 16S ribosomal RNA sequencing (Eckburg et al., *Science,* 308(5728): 1635-38, 2005; Hayashi et al., *Microbiol. Immunol.* 46(8): 535-48, 2002; Turnbaugh et al., *Nature* 457(7228): 480-84, 2009) or metagenomic sequencing (Segata et al., *Nat. Methods,* 9(8): 811-14, 2012). Further data analysis can be used to generate cluster signatures of enterotypes clusters (Culligan et al., *Virulence* 5, 399-412, 2014; Koren et al., *PLoS Comput. Biol.* 9: e10028632013).

A key aspect of the present invention is to employ commensal gut bacteria to pre-condition a subject's immune system to the anticancer activity of OV therapy. Provided herein are methods and combination therapies using gut microbiota to augment the anticancer potential of OV therapy. By using the augmenting commensal gut microbiota approach disclosed herein, this invention can address the boosts that are necessary for the durable response and complete response rates.

SUMMARY OF THE INVENTION

The present disclosure provides therapeutic methods for treating and preventing cancer by augmenting systematic treatments through certain commensal gut bacterial genera, including, but not limited to *Bifidobacterium* and *Bacteroides*, which can potentially boost systemic immune response within the host. These species exhibit significant anti-tumor synergies with checkpoint inhibitors CTLA-4, PD-1/or PDL-1 antibodies when tested in melanoma and colon cancer models or analyzed using melanoma patient samples. Checkpoint inhibitor therapies work by modulating the systemic immune response, one of the two mechanisms underlying OV-based therapies. This invention provides novel methods and combination therapies using OV and commensal gut bacteria species, whose composition in a patient's gut can be further modulated by herb medicine or extracts. This invention also provides methods for building elite responder selection platforms through hierarchical clustering analysis of genomic profiles for human gut microbiome. This invention is applicable to other live therapies (e.g. somatic cell and stem cell therapies), where efficacy relies on systemic activation of the host immune system.

In some embodiments, the present disclosure provides a method of treating and/or preventing cancer comprising administering to a subject an effective amount of gut microbiota, and administering to the subject an effective amount of an oncolytic virus having anticancer activity and that selectively targets tumor cells, wherein the gut microbiota pre-conditions the subject's immune system to antitumor responses and augments the anticancer activity of the oncolytic virus. In certain embodiments, the oncolytic virus is a virus within the poxviridae family. The oncolytic virus may be, but is not limited to, an orf virus, bovine papular stomatitis virus, pseudocowpox virus, or vaccinia virus. In preferred embodiments, the gut microbiota is of the genus *Bifidobacterium*.

Therapeutic methods are provided for the treatment and/or prevention of cancer, including tumor treatment, and treatment for inflammatory conditions. In some embodiments, the cancer is a type of cancer having a high degree of de novo mutations. Preferably, the cancer is melanoma, lung cancer, kidney cancer, glioma, triple negative breast cancer, or renal cancer.

In some embodiments, the oncolytic virus is administered to a subject from about one week to two months after the gut microbiota is administered. Preferably, the oncolytic virus is administered about one month after the gut microbiota is administered. In the methods and uses provided herein, the subject is an animal. Animals can be non-human animals, mammal, or can include humans. In some embodiments, gut microbiota is administered to human subjects at an effective amount of about $10^9$ to $10^{11}$ cfu. The OV may be administered to human subjects at an effective amount from about $10^5$ to $10^{10}$ pfu.

The methods and kits provided herein rely on a pre-condition created by the gut microbiota to enhance the anticancer activity of the oncolytic virus. In some embodiments, the anticancer activity of the OV is synergistically enhanced by the gut microbiota. The critical pre-condition for an effective antitumor response is an enhanced immune response, which may be achieved through commensal gut microbiota augmentation, one of the key concepts of this current invention.

In certain embodiments, a platform is used to identify potential elite responders to the cancer treatment based on an abundance of the subject's particular gut microbiota. The platform is built through hierarchical clustering analysis of genomic profiles of the human gut microbiome. The platform identifies gut microbiota that suppress tumor progression. The pre-screened subject is predicted to respond favorably to an oncolytic virus based on the abundance of the subject's particular gut microbiota.

In some embodiments, combination therapies using gut microbiota and OV therapies are packaged as a kit. The packaged kit may contain instructions for administration and other reagents for administration. In certain embodiments, a kit is provided for the treatment of cancer, comprising a pharmaceutical composition comprising gut microbiota that pre-condition a subject's immune system to antitumor responses, a pharmaceutical composition comprising an oncolytic virus having anticancer activity and that selectively targets tumor cells, instructions for sequentially administering the gut microbiota and oncolytic virus, and wherein the gut microbiota augments the anticancer activity of the oncolytic virus. In some embodiments, the kit is used where the cancer is a type of cancer having a high degree of de novo mutations. The cancer may be melanoma, lung cancer, kidney cancer, glioma, triple negative breast cancer, or renal cancer. The kit may also comprise the gut microbiota, *Bifidobacterium*.

DETAILED DESCRIPTION

Figure 1:
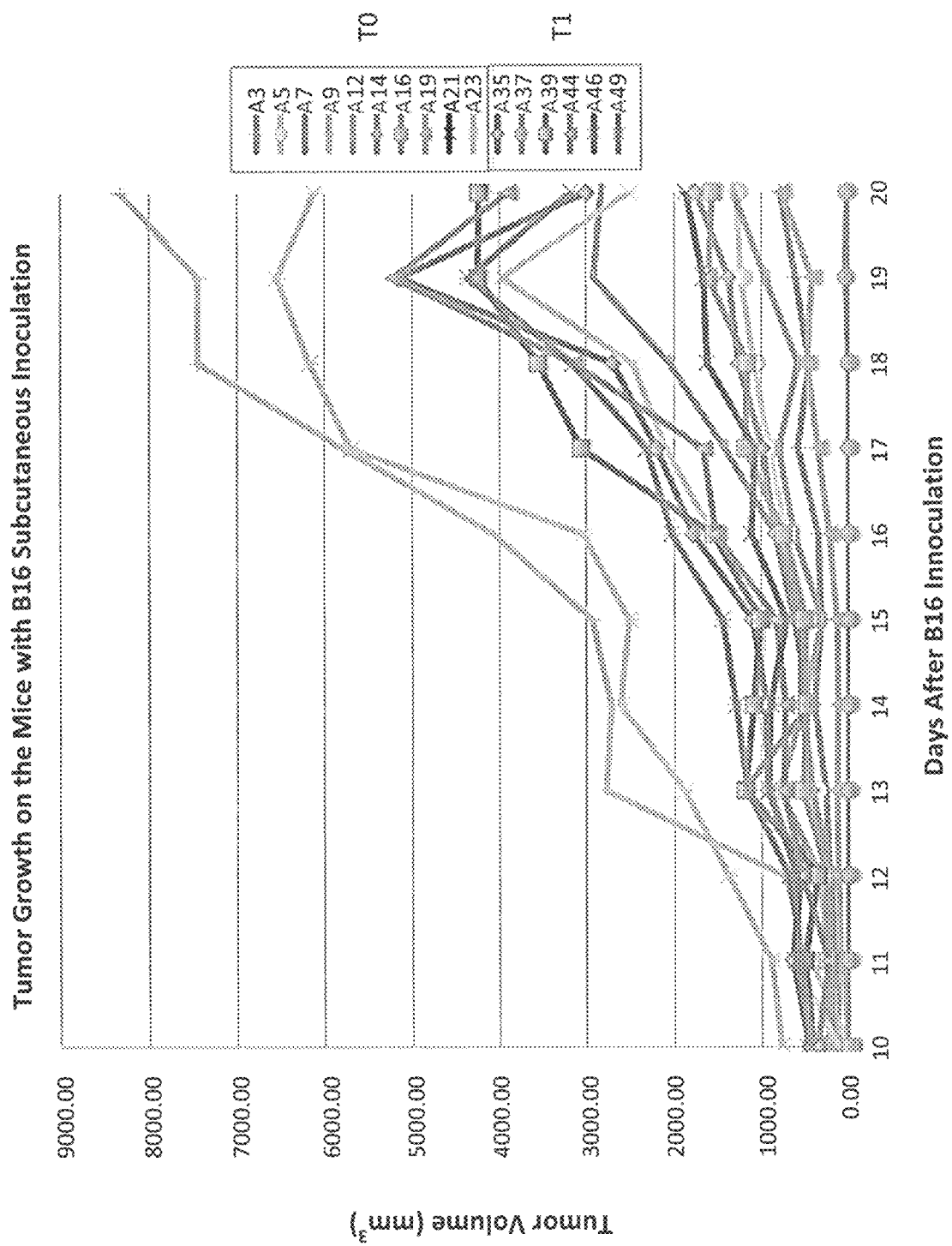
FIG. 1 shows that tumor growth is influenced by the ablation of gut microbes.

The following detailed description and examples illustrate certain embodiments of the present invention. Those of skill in the art will recognize that there are numerous variations and modifications of this disclosure that are encompassed by its scope. Accordingly, the description of certain embodiments should not be deemed as limiting.

All references cited herein, including, but not limited to, published and unpublished applications, patents, and literature references, are incorporated herein by reference in their entirety and are hereby made a part of this specification.

More than 40 oncolytic viruses (OVs) have been evaluated for their therapeutic potential in pre-clinical and clinical studies (Miest & Cattaneo, *Nat. Rev. Microbiol.* 12(1): 23-34, 2014; Buijs et al., *Hum. Vaccin. Immunother.* 11(7): 1573-84, 2015; Patil et al., *J. Contemp. Dent. Pract.* 16(8): i-ii, 2015; Kaufman et al., *Nat. Rev. Drug Discov.* 14(9):

642-62, 2015). Disclosed herein are OV combination therapies containing gut commensal bacteria species. In certain embodiments, the combination therapy comprises the orf virus (ORFV) due to its documented safety profile as well as its unique ability to cause repeat infections. In addition, ORFV exhibits an ability to induce robust stimulatory immune responses with the special involvement of natural killer (NK) cells and dendritic cells (DCs), and ORFV's replicative "niche" has an extensive vasculature, similar to a tumor microenvironment, which has beneficial effects on its anti-tumor activity (Rintoul et al., *Mol. Ther.* 20(6): 1148-57, 2012; Rziha et al., *Methods Mol. Biol.* 2016; 1349:177-200, 2016). Furthermore, ORFV shows superior in vivo anti-tumor activities in immunocompetent murine lung cancer models and in human lung cancer xenograft models. In some embodiments, ORFV recombinants containing either reporter or anti-tumor enhancing genes are designed to facilitate ORFV tissue distribution and biopsy analysis and boost ORFV's antitumor activity. In another embodiment, ORFV is the main component of a combination antitumor treatment containing an augmenting agent.

In some embodiments, in vivo ORFV monitoring is carried out by a recently developed technology (Rziha et al., *Methods Mol. Biol.* 2016; 1349:177-200, 2016) that rapidly detects ORFV viral load and the delayed re-emergence of its genomes in the blood. Positive readout at an extended time point after ORFV administration indicates intratumoral viral replication and subsequent leakage into the systemic circulation, suggesting a more potent anti-tumor reaction. In a preferred embodiment, the therapeutic potential of the ORFV-containing combination treatment is evaluated by analysis of tumor burdens and animal survival rate of the testing subjects. Other viral species for evaluation include, but are not limited to, species within the poxviridae family, for example, a vaccinia virus (VACV), named POV-801 in this invention.

OV treatment alone usually exhibits low antitumor efficacy, in terms of both the population response rate and individual patient recovery, which has been observed in both in preclinical and clinical studies (Kirn, *Gene Ther.* 8(2): 89-98, 2001; Kelly & Russell, *Mol. Ther.* 15(4), 651-59, 2007; Burke et al., *Curr. Opin. Virol.* 13:55-60, 2015; Harrington et al., *Expert Rev. Anticancer Ther.* 15(12): 1389-403, 2015; Kaufman et al., *Nat. Rev. Drug Discov.* 14(9): 642-62, 2015; Patil et al., *J. Contemp. Dent. Pract.* 16(8): i-ii, 2015; Seymour & Fisher, *Br. J. Cancer* 114(4): 357-61, 2016). Therefore, disclosed herein are methods of creating favorable anti-tumor immune conditions within a test subject with an agent, such as the gut commensal bacteria, to create this pre-condition. In a particular embodiment, a variety of gut commensal bacterial species are evaluated for augmenting the antitumor activity of the selected OVs. In a preferred embodiment, the gut bacteria genus is *Bifidobacterium*. Certain bacterial species within this genus have also been used to ameliorate clinical symptoms of irritable bowel syndrome and inflammatory and necrotizing enterocolitis (Ng et al., *Inflamm. Bowel Dis.* 15, 300-10, 2009; Gareau et al., *Nat. Rev. Gastroenterol. Hepatol.* 7, 503-14, 2010) based on its ability to modulate the balance of the gut microbiota (Etzold et al., *Environ. Microbiol.* 16, 888-903, 2014). The safety and benefits of *Bifidobacterium* in preventive medicine have been well documented, and its composition can fluctuate in the range of ~6% to ~36%.

In some embodiments, *Bifidobacterium*'s potential augmenting effects to a selected OV are evaluated in preclinical studies. In other embodiments, in vivo monitoring of *Bifidobacterium* is performed using a modified terminal restriction fragment length polymorphism (T-RFLP) analysis of test subject's fecal samples (Nagashima et al., *Biosci. Microflora.* 25: 99-107, 2006). The physiological effects of *Bifidobacterium* may also be evaluated using various in vitro assays. In certain embodiments, the augmenting effect of *Bifidobacterium* is assessed by comparing the tumor burden and survival rate of the test subjects treated with OV by itself as well as OV with *Bifidobacterium*. Other gut commensal bacteria species for evaluation include, but are not limited to, those published by the World Gastroenterology Organization or species discovered through the disclosed hierarchical clustering studies.

In other embodiments, the immunomodulatory effects of herb extracts or medicines that can regulate the composition and function of the gut commensal bacteria species are tested.

In certain embodiments, human clinical trials of successful agent-containing combination OV therapy are designed following the completion of pre-clinical studies. In a preferred embodiment, enrolled patients are unresponsive to current antitumor therapies and are potential "elite responders" based upon the disclosed hierarchical clustering analysis platform.

In certain embodiments, the OV is administered to human subjects about one week to two months after the gut commensal bacteria are administered. In a preferred embodiment, the OV is administered to human subjects about one month after the gut commensal bacteria are administered. In mice, the oncolytic virus is administered about one to two weeks after the gut commensal bacteria are administered. In some embodiments, an effective amount of the gut microbiota is from about $10^9$ to $10^{11}$ cfu. In still other embodiments, an effective amount of the oncolytic virus is from about $10^5$ to $10^{10}$ pfu.

As part of this disclosure, at least 2 tubes of orf virus comprising virus POV-601 have been deposited and made available to the public without restriction (but subject to patent rights), with the China Center for Type Culture Collection (CCTCC), Wuhan University, Wuhan 430072, China. The deposit, designated as CCTCC Deposit No. V201713, was made on behalf of Minjie Hu on Mar. 28, 2017. This deposit was made and will be maintained in accordance with and under the terms of the Budapest Treaty with respect to seed deposits for the purposes of patent procedure.

In some embodiments, the combination therapies are evaluated in human disease, particularly cancer. There are more than 200 types of human cancers (ACS (2015) Global Cancer Facts & Figures). Some cancer types contain a high degree of de novo mutations, which encode neoantigens of the clinical failure key drivers. Certain neoantigens that reside in the cells of spatially separated intratumoral subclones within a solid tumor are released out upon OV's oncolysis. The released neoantigens could be presented by a set of antigen presenting cells (APC), like the dendritic cell (DC), and a whole panel of immunity against these neoantigens will be initiated, leading to a potent eliminating action to all the existing cancer cells harboring different neoantigens. Disclosed herein are methods of increasing the efficacy of neoantigen presentation and immunity induction by pre-conditioning a host's immune system with a selected augmenting agent, generating strong systemic antitumor responses. In some embodiments, the method is used for, but not limited to, high mutation cancer types including melanoma, lung cancer, kidney cancer, glioma, triple negative breast cancer, and renal cancer. Melanoma and lung cancer patients, compared to patients with other types of cancers, respond favorably to immune checkpoint inhibitors (Ipilimumab, Nivolumab, and Pembrolizumab) and to the oncolytic virus therapy T-VEC, which manifests through prolonged survival rates. In a preferred embodiment, the combination therapy is used to treat lung cancer. In other embodiments, the combination therapy is used to treat high-mutation cancer types. In still other embodiments, the combination therapy is used to treat cancer types having normal or low mutation rates.

Figure 6:
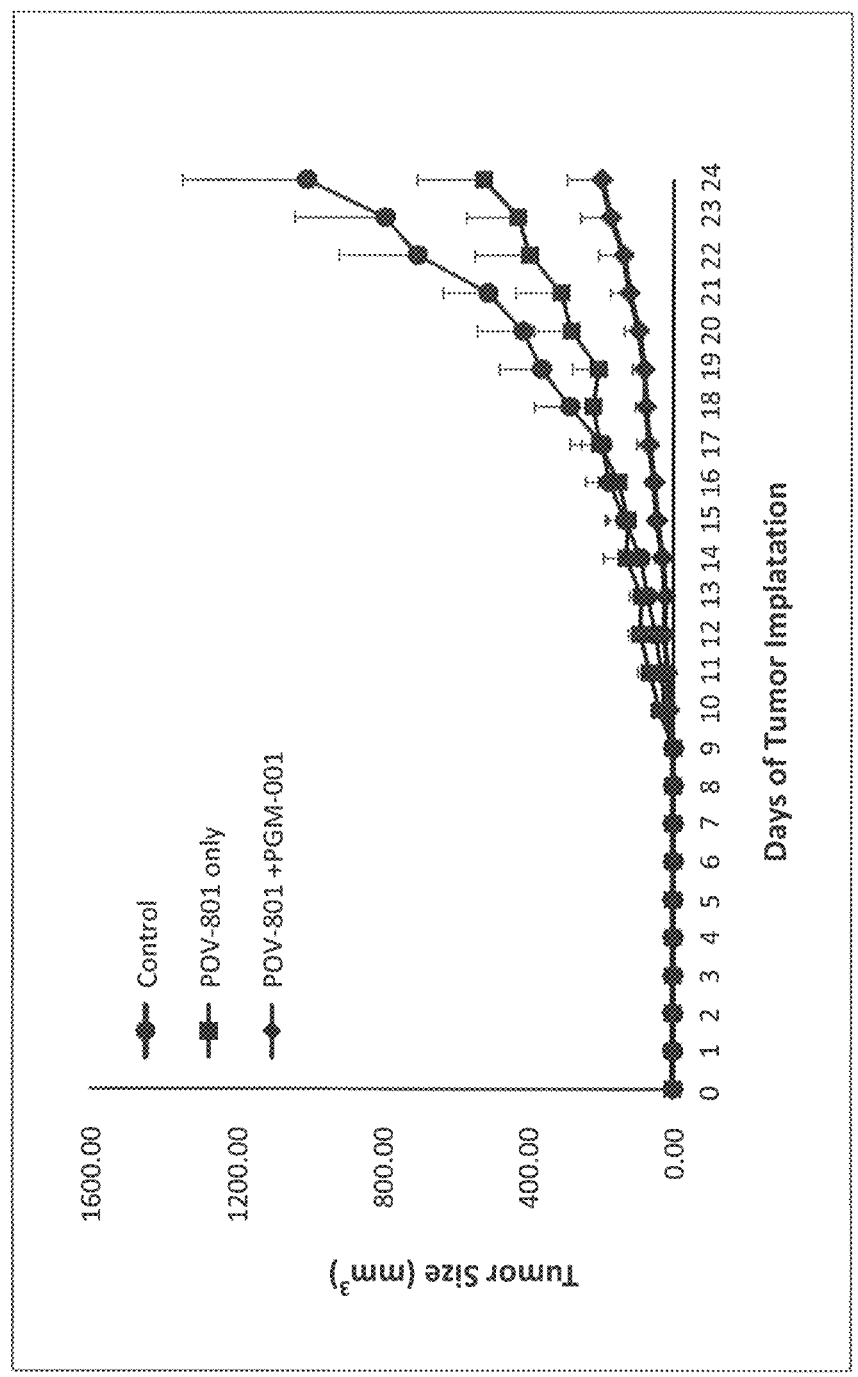
FIG. 6 shows the synergistic anti-tumor activity of an OV/GM (POV-801+PGM-001) combination in a syngeneic murine melanoma tumor model.
Figure 7:
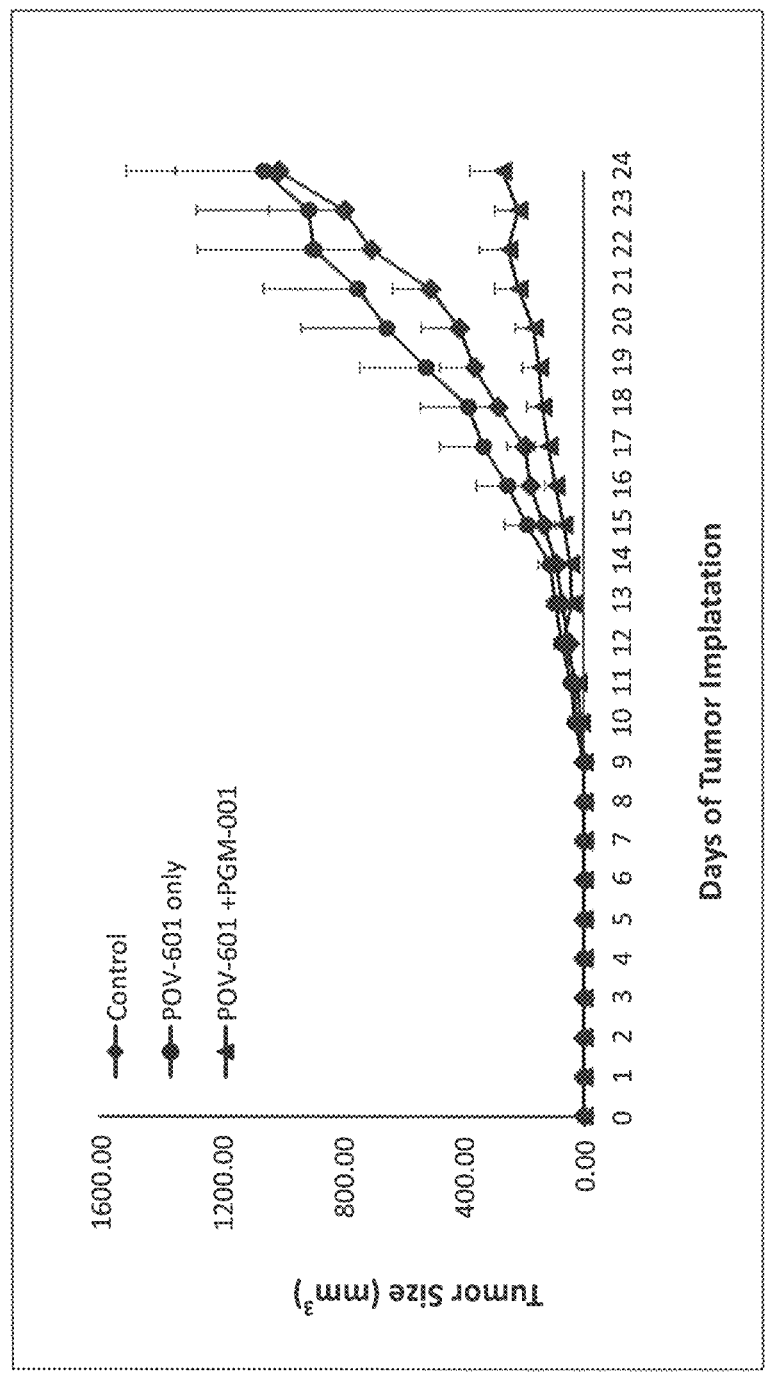
FIG. 7 shows the synergistic anti-tumor activity of OV/GM (POV-601+PGM-001) combination in a syngeneic murine melanoma tumor model.
Figure 8:
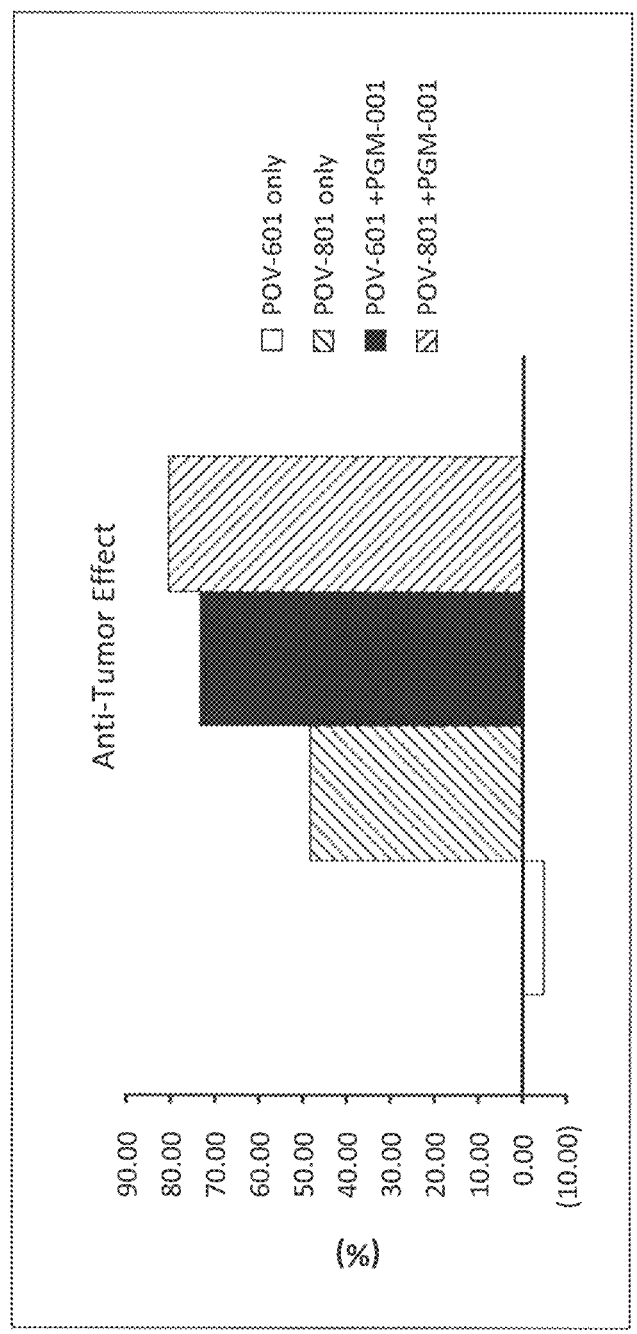
FIG. 8 shows the synergistic anti-tumor effects of various OV/GM combinations in a syngeneic murine melanoma tumor model.
Figure 11:
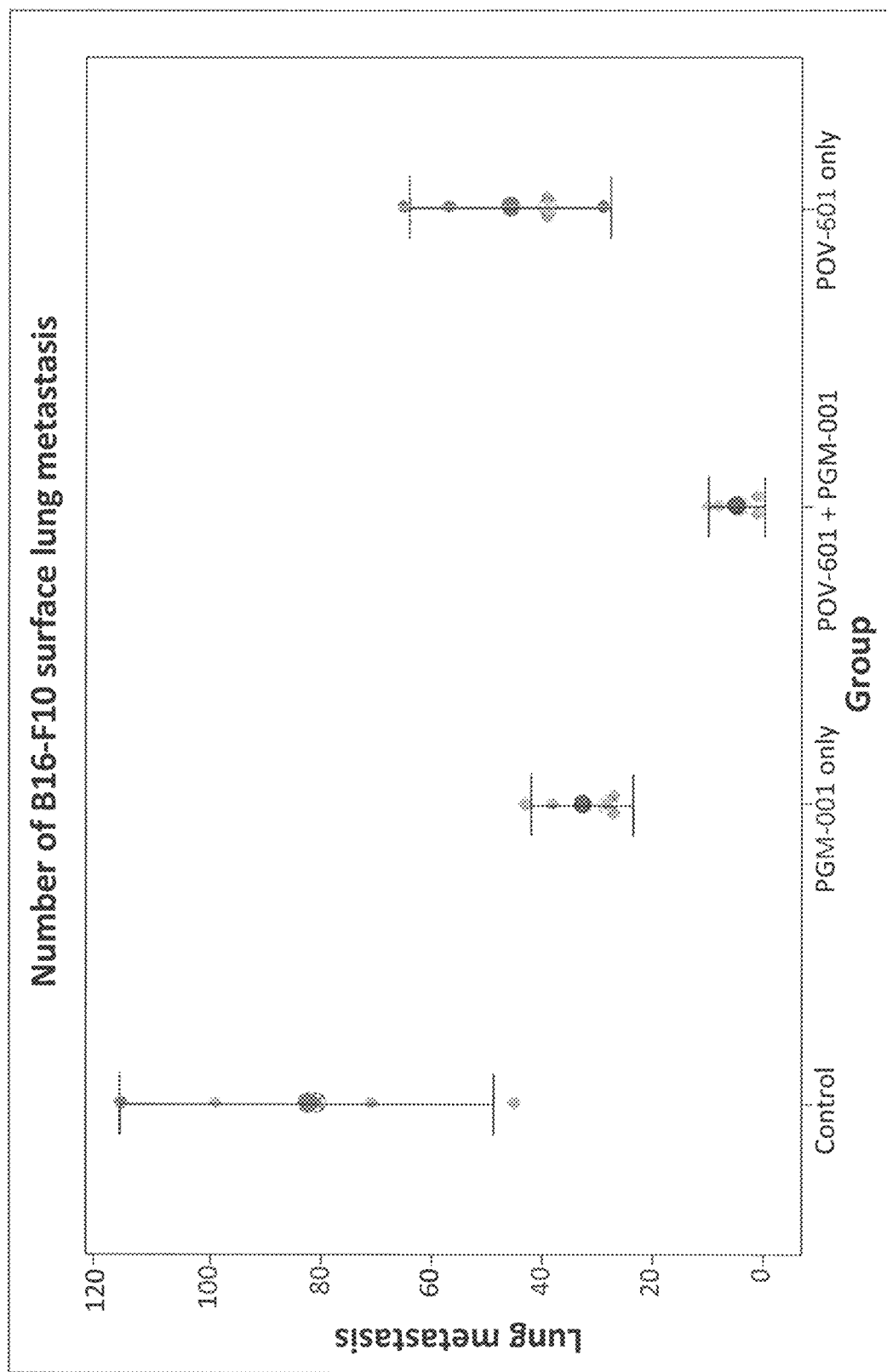
FIG. 11 shows the synergistic anti-tumor activity of OV/GM (POV-601+PGM-001) combination in a murine lung tumor model.

In some embodiments, antitumor responses are evaluated in preclinical studies using selected animal models. Various murine models that have been developed to examine responses to a developing therapy may be used herein. These experimental mouse models include, but are not limited to, models falling within three main categories: transplantable tumors, genetically engineered/transgenic models, and humanized mouse xenograft models. Transplantable tumor models are the most widely used in cancer preclinical studies due to rapid output. On the other hand, transgenic models confer greater phenotypic variability, and xenograft experiments are usually performed in either nude or severe combined immunodeficiency (SCID) mice that are deficient in adaptive immunity. In certain embodiments, pre-clinical evaluation of the disclosed combination therapies are evaluated in multiple tumor models. In other embodiments, transplantable models are designed to observe the adaptive immune response. In these models, mouse strains have the identical genetic backgrounds to that of the transplanted cancer cell lines. An example of this transplantable model is C57BL/6 house mice challenged intravenously with a murine B16-F10 melanoma cancer cell line to create a lung metastasis cancer model whose adaptive immune response can be monitored. In certain embodiments, the tumor-bearing animals of the transplantable model studies are administered with or without the selected augmenting agent, followed by application of the testing OV, and harvesting and processing their lungs for tumor burden analysis, as shown in FIG. 11 this invention. In other embodiments, a fluorescently labeled human lung cancer cell line, including but not limited to A549, is engrafted subcutaneously into the flank of a nude mouse strain, including but not limited to CD1, to create a human lung cancer xenograft model. In certain embodiments, the murine B16-F10 melanoma cell line was subcutaneously injected into the right flank of a C57BL/6 mouse, and tumor volumes are measured using digital calipers following administration of the augmenting agent and the testing OV, as shown in FIGS. 6,7,8. In certain embodiments, the augmenting immune responses are initially assessed by counting total numbers of splenic NK, DC, and $CD8^+$ T cells or by analyzing the expression levels of certain lymphocyte activation markers (e.g. CD69, CD80 and CD 86) and immune responding cytokines (e.g. interleukin-1β (IL-1β), granulocyte-macrophage colony-stimulating factor (GM-CSF), IL-2, IL-6, TNF-α and IFN-α) before and after agent administration. In some embodiments, the tumor burden and animal survival analysis are assessed. In other embodiments, preclinical tumor models for other types of cancers are created and used to evaluate the disclosed combination therapies. Data generated from the preclinical studies provide useful safety and efficacy information about the disclosed combination therapies and guide the design of human clinical trials.

All selected augmenting agents and oncolytic viruses are formulated following Good Laboratory Practice (GLP) and Good Manufacturing Practice (GMP) guidelines. In certain embodiments, the augmenting bacterial agents are obtained from a commercial resource or human fecal samples. In some embodiments, commercially obtained bacteria in live forms are expanded on reduced clostridial medium (RCM) agar in anaerobic conditions. The bacteria obtained may be formulated in phosphate-buffered saline (PBS) at $5 \times 10^6$ c.f.u./µl. Before OV application, a starting dose of 200 µl formulated bacteria is administrated to each mouse through oral feeding based on published data (Sivan et al., *Science* 350(6264): 1084-89, 2015). The total amount of formulated bacteria is given either in a single dose or in multiple doses spread out over several days (e.g. 14 days), and the frequency and duration of dose administration is determined.

The oncolytic viruses are formulated either in PBS with 10% v/v glycerol or in 30 mM Tris with 10% (w/v) sucrose at a viral concentration of $10^5$ p.f.u./µl. Although the accurate dosage of an OV is dependent on its virulence and the nature of the targeting tumor, an initial dose of $10^7$ p.f.u. is administered to each mouse based on published data (Rintoul et al., *Mol. Ther.* 20(6): 1148-57, 2012). The viral formulation is administered either locally or systemically, depending on the animal model. Since the first OV drug T-Vec was successfully delivered through local injection (Harrington et al., *Expert Rev. Anticancer Ther.* 15(12): 1389-403, 2015), the same approach can be used in this invention. In certain embodiments, up to five doses of 100 µl viral formulation are injected intratumorally at different time points, and the treated tumors are measured 2-3 times per week using digital calipers. Systemic delivery has the benefit of evaluating adaptive immune response, which is critical for treating a metastatic tumor. In other embodiments, mice are treated intravenously with five doses of 100 µl viral formulation and are monitored for signs of organ distress. To aid in administration in clinical studies, the selected bacterial agent(s) and the chosen oncolytic virus(es) may be formulated as an ingredient in a pharmaceutical composition separately. Therefore, in some instances, the compositions may routinely contain pharmaceutically acceptable concentrations of salt, buffering agents, preservatives and various compatible carriers. The proportion and identity of the pharmaceutically acceptable diluent depends on the chosen route of administration, compatibility with a live virus and, where applicable, compatibility with the stability of the immune-augmenting agent. Starting doses of $3 \times 10^7$ c.f.u. kg-1 of the selected bacterial agent and $1 \times 10^7$ p.f.u. kg-1 of the chosen virus in formulated forms are used based on published clinical studies (Kaufman et al., *Nat. Rev. Drug Discov.* 14(9): 642-62, 2015; Waller et al., *Scand. J. Gastroenterol.* 46: 1057-64, 2011). For systemic delivery studies, the formulated virus is diluted in bicarbonate-buffered saline in a total infusion volume of 50 ml immediately before intravenous infusion, and is infused over the course of 60 min. Tumor response is assessed by contrast-enhanced computed tomography (CT) imaging, maximum tumor diameters, and Hounsfield units (Breitbach et al., *Nature* 477, 99-102, 2011).

The current invention also aims to build a platform for the selection of elite responders to individual OV therapy. In certain embodiments, fecal samples are collected from a group of 60 consented subjects divided into three categories: cancer patients, non-disease subjects in a high-risk population, and healthy subjects in a low-risk population. The microbial DNA in each sample is purified with methods modified from the protocol of American Human Microbiome Project (HMP) (Wesolowska-Andersen et al., *Microbiome*, 2, 19, 2014). Following DNA purification, the quality of the DNA is checked with a spectrophotometer, and only DNA with a 260 nm/280 nm ratio higher than 1.8 is subject to 16S ribosomal RNA target sequencing or metagenomic sequencing.

PCR amplification of the 16S RNA gene is conducted with primers designed based on the conserved regions across all bacterial strains, and the PCR products are purified with the QiaQuick PCR purification kit from, but not limited to, Qiagen. In certain embodiments, the PCR-amplified 16S ribosomal RNA (rRNA) target sequencing is performed. In other embodiments, the abundance of species-specific sequences of the variable regions of rRNA is utilized for clustering analysis. In comparison to 16S rRNA sequencing, metagonomic sequences enable exploration of thousands of species. In some embodiments, reads from metagenomic sequencing are mapped to the strain-specific sequences from the bacterial genome databases built from 3000 reference genomes (Grice & Segre, *Annu. Rev. Genomics Hum. Genet.*, 13, 151-70, 2012; Human Microbiome Jumpstart Reference Strains et al., 2010). The reference genomes are indexed with a Burrows-Wheeler index. The mapped data are normalized based on the length of reference sequences and total read counts. The calculated abundances of bacterial strains are further subjected to clustering analysis.

In certain embodiments, the bioinformatics tools developed by R statistic programming are used to generate a taxonomic tree (Segata et al., *Nat. Methods*, 9(8): 811-14, 2012) and an enterotype cluster for each person. In other embodiments, tumor-bearing mice are individually pre-treated with each collected human fecal sample, followed by a treatment with a chosen OV (e.g. ORFV). The tumor burden and animal survival rate in each testing mouse are monitored and analyzed to generate a set of anti-tumor efficacy data. Following a comparison analysis of all the "positive" taxonomic trees and enterotype clusters from persons having the positive antitumor efficacy data and certain mathematic calculations, one platform is built for selection of potential elite responders to the chosen OV. In other embodiments, the number of human participants is increased to build similar platforms for other OV therapies. In some embodiments, new gut commensal bacteria species may be identified during the comparison analysis. According to this disclosure, the elite responder selection platform can facilitate the development of personalized precision medicine.

"Gut microbiota," "gut commensal bacteria," "gut microbes," or "GM" refer to an ensemble of microorganisms that reside in various organs, preferably the intestines and/or stomach. Gut microbiota contain tens of trillions of microorganisms. In some embodiments, gut microbiota are common to most individuals, while in other embodiments, gut microbiota are specific to an individual.

The phrase "anticancer activity" or "antitumor activity" refers to the ability of an agent to kill cancer cells, decrease the severity of the cancer, or block or prevent the cancer from spreading.

An "effective amount" of an oncolytic virus is meant as an amount sufficient, upon single or multiple dose administration, to treat a cancer cell, prolong or prevent advancement of the cancer (e.g. prevent additional tumor growth of a cancer, prevent additional inflammatory response), ameliorate, alleviate, relieve, or improve a subject's symptoms of the cancer beyond that expected in the absence of such treatment. The amount of oncolytic virus required may depend on the particular virus given, the type of cancer being treated, the route of administration, and the length of time required to treat the cancer. It should also be understood that a specific dosage and treatment regimen for any particular patient will depend upon a variety of factors, including the activity of the oncolytic virus, the age, body weight, general health, sex, diet of the patient, time of administration, rate of excretion, drug combinations, the judgment of the treating physician, and the severity of the particular cancer being treated. In certain aspects where the oncolytic virus is administered in combination with gut microbiota, the amount of additional oncolytic virus present in a composition of this invention typically will be no more than the amount that would normally be administered in a composition comprising that oncolytic virus as the only active agent.

"Pre-condition" refers to a process of administrating a set of gut microbes to test subjects ahead of OV treatment. The intake of gut microbes interrupts the subject's immunological equilibrium that pathologically favors tumor progression. The gut microbes also enhance the subject's immune system to recognize tumor-specific signals released from OV-targeted cells. A systematic immunological response to tumor loci is boosted after administration of gut microbes.

The term "intratumoral" refers to the space within a tumor. The mechanism of pre-conditioning is critical for an effective antitumor response. In certain embodiments, a "pre-conditioned" state facilitates the killing of metastatic cancer cells at distant sites previously unseen by a virus and intratumoral bystanders localized outside of the infected area.

An "effective amount" of a gut microbiota is an amount sufficient to create the "pre-condition," and thus facilitates an effective antitumor response.

EXAMPLES

The following examples are intended to be illustrative and in no way limit the scope of the disclosure.

Example 1—Gut Microbiota Experiments

A. Isolation of the Microbial Strains

Isolation and Purification of Prajna's Microbial Strains

A specific bacterial strain is purified by separation of a single bacterial colony from the bacterial culture. A starting probiotic material containing several bacterial strains was cultured with serial dilutions on solid agar culture plates. These plates contained well-separated colonies, from which single colonies were picked up, each representing individual strains. Each picked colony was streaked onto fresh plates and incubated for 24-72 hours (strain-dependent) at 37° C. to allow the formation of a new individual colony. The process was repeated multiple times to ensure that the bacteria within a colony originated from a single clone. The final colonies were used to expand the selected bacterial strains.

B. Microbial Culture

Equipment Set Up and Configuration

To begin an anaerobic culture, the culture chambers of a Work Station were filled with mixed gases. The components of the mixed gases are nitrogen (80-90%), carbon dioxide (5-10%) and hydrogen (5-10%). The catalyst palladium (Pd) was used to remove the trace oxygen by enabling a reaction between oxygen and hydrogen.

Preparation of a De-Gas Broth

An autoclaved culture broth was continuously flushed by filtered nitrogen gas for 30-60 minutes until the color of the oxygen indicator (0.3% resazurin) changed from pink to colorless. The de-gassed broth bottle was then capped and sealed with parafilm to prevent air leakage. All the broths were used within the culture chamber of a Work Station.

Strain Stocks Preparation 14 ml bacterial culture from individually selected colonies was mixed with 14 ml of 30% glycerol in water, and aliquoted into 2 ml stocks. The stocks were kept at −80° C.

C. Expansion of the Selected Strains and Test of Microbial Growth

100 µl of a strain stock was inoculated into a 50 ml centrifuge tube containing 50 ml of a liquid culture broth, followed by incubation at 37° C. between 24-72 hours (strain-dependent). The 50 ml culture was then transferred into a 1 liter glass bottle containing 1000 ml of liquid culture broth, and allowed to continue growth at 37° C. between 24-72 hours. The growth property of each selected strain was evaluated by performing growth curve experiments. 3 ml sample was taken from a 50 ml tube containing 50 ml bacterial culture at sequential time points, and OD (optical density) value at 600 nm was measured by a plate reader. A growth curve for each strain was plotted (OD read vs. time) and the log growth phase for each strain was determined. The log phase culture of each strain was used for the preparation of animal administration solutions.

D. Quantification of the Selected Microbial Strains

To quantify the titer of a selected bacterial strain, a serial dilution culture was set up. A glycerol stock of a bacterial strain was serially diluted to the concentrations of 10X, $10^2$X, $10^3$X, $10^4$X, $10^5$X, $10^6$X. The diluted bacteria were cultured on solid agar plates. The number of the colonies on each plate was counted and the titer of original bacterial stock was calculated by multiplying the count and dilution factor.

E. Preparation of the Bacteria Administration Solutions for Animal Studies PGM-001

2 ml of sterile PBS was added to a 50 ml centrifuge tube containing one capsule (440 mg/capsule) of a probiotic powder and stirred for 6 minutes with a sterile glass stick to re-suspend the powder. The suspension was then centrifuged at 500 rpm for 2 minutes to let the wall-adhered suspensions down to the tube bottom, which is the PGM-001 administration solution with a cfu at $5 \times 10^9$/ml.

All the tubes containing individual administration solution were filled with nitrogen gas and kept at room temperature less than 60 minutes before animal administration.

F. Molecular Detection and Speciation of Microbial Species

Detection of Bacterial Strains with PCR and 16S Sanger DNA Sequencing

The genomic sequences from different species can provide distinguishing signatures for species differentiation. The 16S rRNA gene sequence can fulfill the task with integrative homologous and clustering analysis of its hyper-variable regions (V1-V9). The 16S rRNA gene was amplified by the polymerase chain reaction (PCR) with the primers: 5'CGG GGG TGC TGC CCA CTT TCA TG3' and 5'GCT TGT TGG TGA CGGT AAC GGC T3'. The PCR product then underwent Sanger sequencing. The sequences started from both ends were processed for assembly of the 16S rRNA gene. The sequences were compared to the microbial genome databases from the NCBI (National Center of Biotechnology Information at National Institute of Health) with the Blastn computational program, and the species with high sequence identity and homology (>99%) to the query sequences in the hyper-variable regions were identified.

qPCR: Primer and Experiment Design qPCR is used as a pre-condition screening with an identified panel of strain specific primers. The quantification of the abundance of rRNA genes in feces could infer the bacterial composition in the gastrointestinal tract. The PCR amplification curve for the panel of bacterial species is utilized for the evaluation of the species composition in the feces. The composition is used to classify the subtypes of tumor bearers.

Genomic DNA is extracted from samples using the Mo Bio Powersoil®-htp 96 Well Soil DNA Isolation Kit (Mo Bio Laboratories, Carlsbad, Calif.) or the QIAamp DNA Stool Mini Kit (QIAGEN, Valencia, Calif.). The thermocycling conditions are set as follows: 95° C. for 2 minutes followed by 45 cycles of 95° C. for 3 seconds, 60° C. for 30 seconds, and subsequent measurement of FAM channel fluorescent readings.

G. Microbial 16S rRNA Gene Sequencing and the Bioinformatics Analysis of the High Throughput Datasets The hyper-variable regions (V3, V4 and V5) of the microbial 16S rRNA gene contain unique strain-specific sequences that can be utilized for studying the microbial lineages. With integrative bioinformatics analysis, phylogeny and taxonomy of the gut microbial species can be elucidated.

The microbial genomic DNA was purified from fecal pellets collected from experimental mice and subject to the high throughput 16S ribosomal RNA (rRNA) gene sequencing by the Illumina sequencing platform. Below is a description of the sequencing data processing.

Selection of Samples for the 16S rRNA Gene Sequencing

The fecal samples from the tumor bearing mice were collected for the bacterial DNA purification. In order to evaluate the effect of gut microbial abundance on the treatment of the tumor, the fecal samples were collected from normal untreated mice as controls, microbial treated, and oncolytic virus treated mice. The fecal samples for each mouse are selected at three time points: before microbial administration, before B16 inoculation, and two weeks after the B16 inoculation. The DNAs were then assessed for the quality control and concentration measurement. Samples passed the quality control are subject to the 16S rRNA gene sequencing downstream.

16S rRNA Gene Sequencing, Data Transfer, and Storage

The hyper-variable regions of 16S rRNA genes were amplified using the following primers:

| Type | Region | Primer Name | Primer (5'→3') |
|---|---|---|---|
| Bacterial 16S | V4 | 515F | GTGCCAGCMGCCGCGGTAA |
| | | 806R | GGACTACHVGGGTWTCTAAT |
| | V3 + | 341F | CCTAYGGGRBGCASCAG |
| | V4 | 806R | GGACTACNNGGGTATCTAAT |
| | V4 + | 515F | GTGCCAGCMGCCGCGGTAA |
| | V5 | 907R | CCGTCAATTCCTTTGAGTTT |

Sequencing platform generated the reads with 250 bp paired-end (PE) with an average of 10,000 reads per sample. The gz-compressed data gzip were transferred through the ftp (file transfer protocol) server.

Raw Data Processing

The sequencing raw reads were pre-processed by demultiplex step of reads, clip step of barcodes, primers and adaptor clips, joining step of paired-end reads. The fastq format was generated for raw reads and pre-processed.

Sequencing Reads QC

The quality control tool, FastQC, is used to assess the sequence files to report base sequence quality, GC content, N base level, sequence duplication level, sequence overrepresentation level, and Kmer content.

Analysis of OTU (Operational Taxonomic Unit) Taxonomy

The pre-processed sequence reads were subjected to the QIIME pipeline for clustering. The sequence reads as input into the pipeline under sequence similarity comparison were then classified into OTUs (Operational Taxonomic Units) with the Greengenes database. With sequence alignment data to the Greengenes references, the abundance of the taxonomic units is evaluated. By comparing the differential abundance between samples with different microbial treatments for the tumor progression, the correlation of the OTU and efficiency of each treatment are identified.

Example 2—Preparation of Oncolytic Viruses for Animal Injection

A. Adenocarcinomic Human Alveolar Basal Epithelial Cell Line A549 Culture

Thaw A549 Cells

A549 Cells (Prajna code: C1; originally obtained from BeNa Culture Collection, Cat #BNCC337696) are thawed by transferring a frozen vial containing $2\times10^6$ cells/ml from a liquid nitrogen tank into a 37° C. water bath. Cell culture medium (10% FBS in DMEM) is warmed in a 37° C. water bath. The vial surface is thoroughly wiped with 75% alcohol. The vial is opened in a cell culture hood and transferred into a 1.5 ml sterile tube with a P1000 pipet. 10 ml of the pre-warmed cell culture medium is slowly added and centrifuged at 230×g for 5 min at room temperature (RT). The supernatant is decanted and the cells are re-suspended in the cell culture medium. The cells are seeded into a 75 cm$^2$ flask at a cell density of $0.7$-$2\times10^6$/flask and placed into a 37° C. cell culture incubator to allow cell growth. The medium is changed the next day.

Subculture of A549 Cells

The cultured cells are viewed under an inverted microscope and the cell confluency is assessed; if the cell confluence is between 50-80%, the next steps are proceeded with. The medium is aspirated and the cell monolayer is rinsed with 10 ml DPBS (without $Ca^{2+}/Mg^{2+}$). 5 ml of 0.25% trypsin/EDTA is added into the rinsed flask. The flask is rotated to make sure that the added trypsin/EDTA covers the cell monolayer. The flask is placed in the incubator for 4-6 minutes. The cells are examined under an inverted microscope to ensure that all the cells are detached and floating. 10 ml of the fresh cell culture medium is added to inactivate the trypsin. The cells are re-suspended with a 10 ml pipet. The cell suspension is transferred into a 50 ml conical tube and the cells are centrifuged at 230×g for 5 min at RT. The supernatant is decanted and the cells are re-suspended in about 5 ml of the cell culture medium. A small aliquot of cells (100-200 µl) is removed and the cells are counted with a Life's cell counter. The cell density is adjusted to $1\times10^6$ cells/ml with the cell culture medium. The re-suspended cells are seeded into T175 flasks at a cell density of $2\times10^6$/flask. The flask is placed into a 37° C. cell culture incubator to allow cell growth, and the medium is changed every other day. The subculture process is repeated as needed.

Cryopreservation of A549 Cells

The cultured cells are viewed under an inverted microscope to make sure that the cell confluence is close to 80%. The A549 cells are harvested and re-suspended with trypsin/EDTA using the steps described above in "Subculture of A549 cells." A small aliquot of cells (100-200 µl) is removed and the cells are counted with a Life's cell counter. The cell viability is examined during cell counting (ideally, the cell viability should be in excess of 90% in order to achieve a good recovery after freezing). The cells are centrifuged at 230×g for 5 min at RT and re-suspended at a density of $1\times10^6$ cells per ml in the cell freeze medium. The cell suspension is aliquoted into 1 ml aliquots in 2 ml cryogenic vials and the vials are placed into a –80'C freezer for 4 hours. The vials are transferred to the gas phase of a liquid nitrogen storage tank and the location of each vial is recorded.

B. Viral Production

Infection of Virus

Virus infection is performed with Prajna code: POV-801, originally obtained from China Center for Type Culture Collection, Cat #GDV117. The cultured A549 cells in a 175 cm$^2$ flask are viewed under an inverted microscope to make sure that the cells have reached confluence. The medium is changed and 200 µl of a viral stock is transferred into the flask. The flask is rotated to ensure that the added viral solution completely covers the cell monolayer. The flask is placed into a 37° C. cell culture incubator to allow viral infection of A549 cells. The viral treated cells are examined every day under an inverted microscope. If over 90% of the cells changed their morphology from a flat to round shape, the infection process is complete.

Cryopreservation of Virus

Infected A549 cells are viewed under an inverted microscope to ensure that the infection process is complete. The culture medium is transferred into a 50 ml conical tube and washed with DPBS. 3 ml 0.25% trypsin/EDTA are added and the flask is placed into a 37° C. incubator for 3 minutes. A small volume of fresh cell culture medium is added to inactivate the trypsin. The cells are centrifuged at 3000 rpm for 10 min at RT and the supernatant is aspirated. The pellet is re-suspended with 10 mM EDTA in PBS and the viral stocks are stored at –80° C.

Viral Release from the Infected Cells

The freezing and thawing of the viral stock is repeated three times. The treated viral samples are sonicated for 3×1 minutes. The sonicated samples are centrifuged at 230×g for 10 min at 4° C. The supernatant is transferred into a 15 ml tube and the remaining pellet is re-suspended with PBS. The supernatant and suspension are placed into a –80° C. freezer.

Preparation of the Cells for Viral Titer Determination

Cell medium is aspirated from an A549 confluent T175 flask. The cell monolayer is rinsed with 10 ml DPBS (without Ca2+/Mg2+). 5 ml of 0.25% trypsin/EDTA are added into the rinsed flask and the flasked is rotated to ensure that the added trypsin/EDTA covers the cell monolayer. The flask is placed in the incubator for 4-6 minutes. The cells are examined under an inverted microscope to ensure that all the cells are detached and floating. 5 ml of fresh cell culture medium is added to inactivate the trypsin. The cells are re-suspended with a 10 ml pipet. The cell suspension is transferred into a 50 ml conical tube. The cells are centrifuged at 230×g for 5 min at RT and the cells are re-suspended in 5 ml of the cell culture medium. A small aliquot of cells (100-200 µl) is removed and the cells are counted with a Life's cell counter. The cell density is adjusted to $1\times10^6$ cells/ml with the cell culture medium. The cell suspension is diluted into $1\times10^5$ cells/ml with the cell culture medium. 2 ml of the cell suspension is transferred into each well of a 6-well plate and the plate is swirled to ensure the even distribution of cells in each well. The cells are cultured in a 37° C. incubator for 2 days.

Viral Titer Determination

A stock of the virus to be tittered is thawed on ice. A serial dilution of $10^2$, $10^3$, $10^4$, ... $10^8$ is prepared. Each well of the cell-seeded 6-well plate is labeled with the corresponding dilution. The medium is aspirated from each well. 1 ml of the viral dilution is transferred into its corresponding well and the plate is incubated in a 37° C. incubator for 60 minutes. The viral inoculum is removed from each well. 2 ml of a freshly made culture medium (2% FBS in DMEM) is added to each well and the plate is incubated in a 37° C. incubator for 2 days. Following the 2-day incubation, 2 ml of a crystal violet solution is added to each well. The dye is allowed to sit on the cells for 10 minutes. The plaque numbers in each well are counted. The following equation is used to calculate the plaque formation unit (pfu):

$$(\text{\# of plaques counted})/(\text{mL of inoculum/well}) \times \text{dilution factor} = \text{pfu/ml}$$

Example 3—Tumor Growth Influenced by Ablation of Gut Microbes

To evaluate the inhibitory functionality of gut microbiota on tumor growth, an assay was developed that showed high bifidobacteriaceae abundance correlated with slower tumor progression. C57BL/6 mice were separated into two groups: T0: No antibiotic treated and T1: antibiotic treated. The mice in both groups had been housed in our SPF facility for 4 days and treated with or without antibiotics for two weeks before 10E6 B16-F10 cells were inoculated subcutaneously. Tumors were measured every day starting from the 10th day after the inoculation. Fecal pellets were collected at two weeks after the B16 inoculation. Data show that tumors generally grow faster on the T1 mice than on most of T0 mice (FIG. 1). This suggests that ablation of gut microbes enhances tumor growth and further implies microbes suppress tumor progression.

Figure 2:
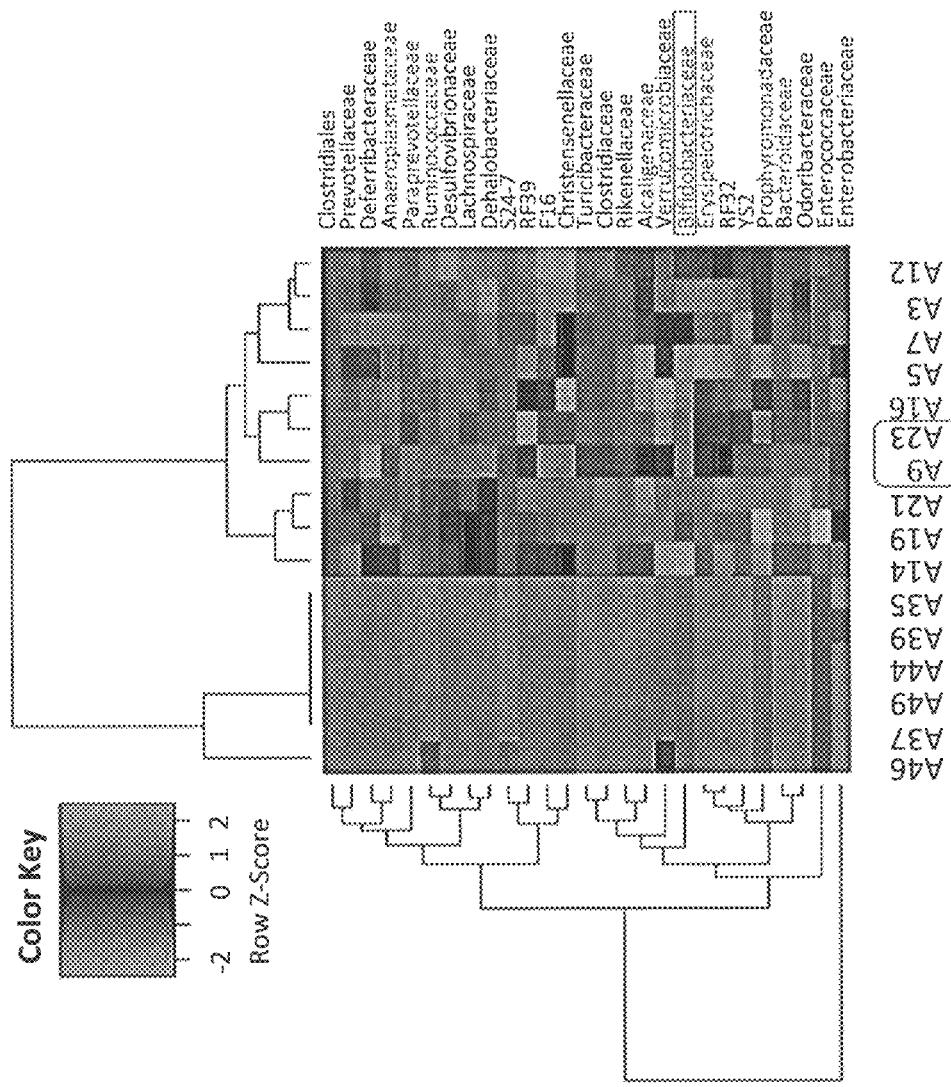
FIG. 2 shows a heatmap of 16S rRNA gene sequencing.

High throughput 16S rRNA gene sequencing was utilized to evaluate the different microbe genus. The microbial genomic DNA was purified from the fecal DNA. The sequencing reads were processed and mapped to the Greengenes databases. The 16S rRNA gene abundances of each microbial genus were evaluated. Further differential abundance was analyzed by using R program DESeq. The normalized read counts were utilized to plot a heatmap with hierarchical clustering method (FIG. 2). FIG. 2 shows that two samples displayed low levels of bifidobacteriaceae (A9 and A23) in the untreated group T0. The analysis was performed with blinded sample labeling.

Figure 3:
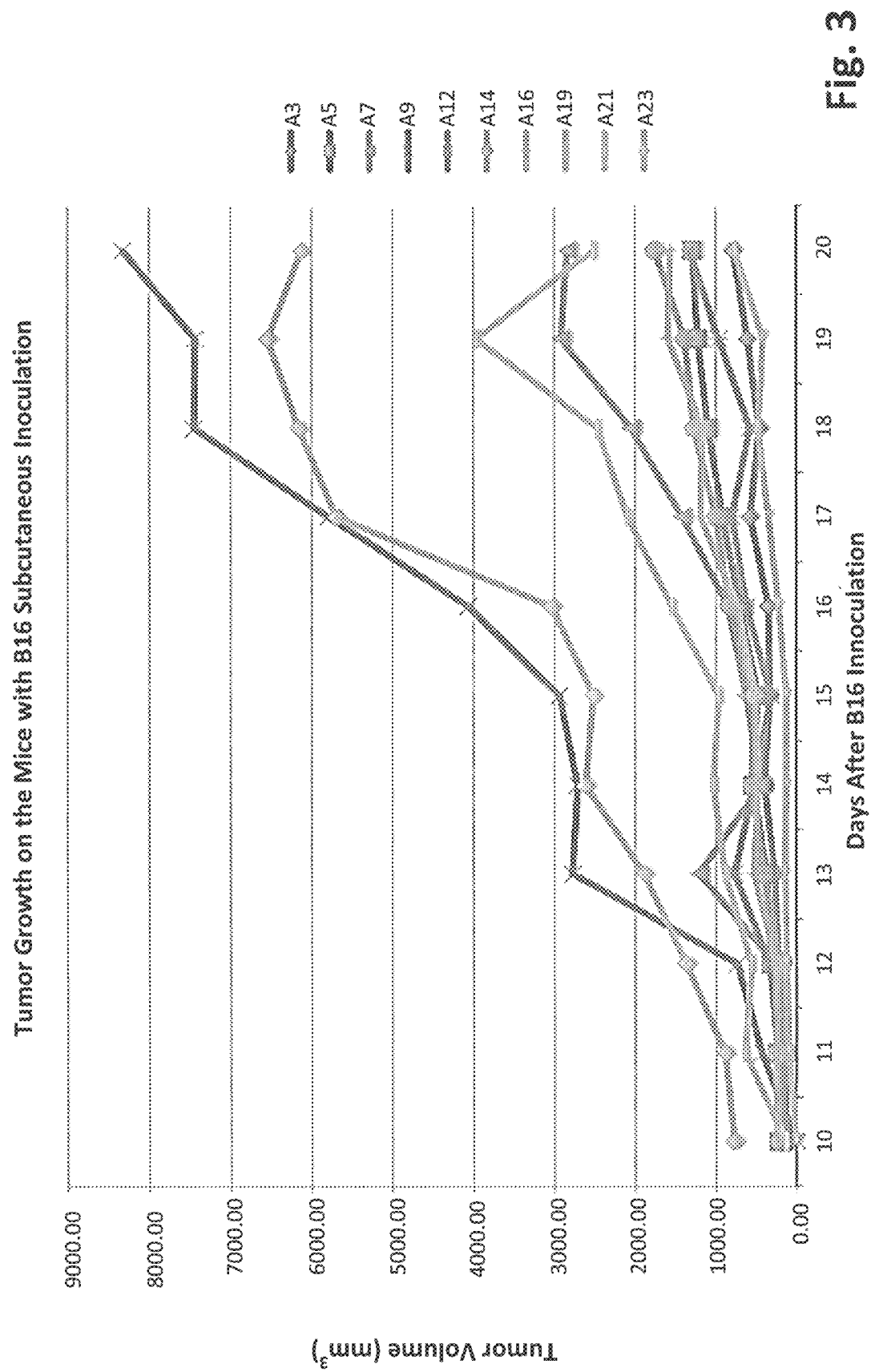
FIG. 3 shows tumor growth curves for mice without antibiotic treatment.

With this information on tumor growth, samples A9 and A23 matched the two mice with exceptional tumor growth (FIG. 3). The experiment revealed that the bifidobacteriaceae played a role in tumor suppression.

Example 4—Evaluation of Acute Toxicity of POV801 and POV601 with Healthy Mice

A. Experimental Design
The experimental design is summarized in Table 1:

TABLE 1

| Group # | Animals # | Oncolytic Virus | Administration Route | Dose |
|---|---|---|---|---|
| 1 | 3 | POV-601 | Subcutaneous | 4 X of the dose used in the anti-tumor study |
| 2 | 3 | POV-601 | Intravenous | 4 X of the dose used in the anti-tumor study |
| 3 | 3 | POV-801 | Subcutaneous | 4 X of the dose used in the anti-tumor study |

B. Procedure and Evaluation
Test Articles and Animals
Test articles include Oncolytic Virus (OV): POV-601: $1 \times 10^8$ PFU/mL; POV-801: $1 \times 10^8$ PFU/mL. POV-601 is from CCTCC Deposit No. V201713. POV-801 was obtained from China Center for Type Culture Collection (Wuhan, China, Cat #GDV117). C57BL/6 female mice, aged between 49~62 days, were supplied from Beijing Vital River Laboratory Animal Technology Co., Ltd. and housed in a standardized animal facility following the Animal Care and Veterinary Services standard operating procedures.

Procedure
A test article was injected into a testing animal either subcutaneously or intravenously at a dose shown in Table 1. Each testing mouse was weighed and the weight was recorded every day until all the testing mice were sacrificed. The mortality, behavior, and body weight were evaluated everyday.

Figure 4A:
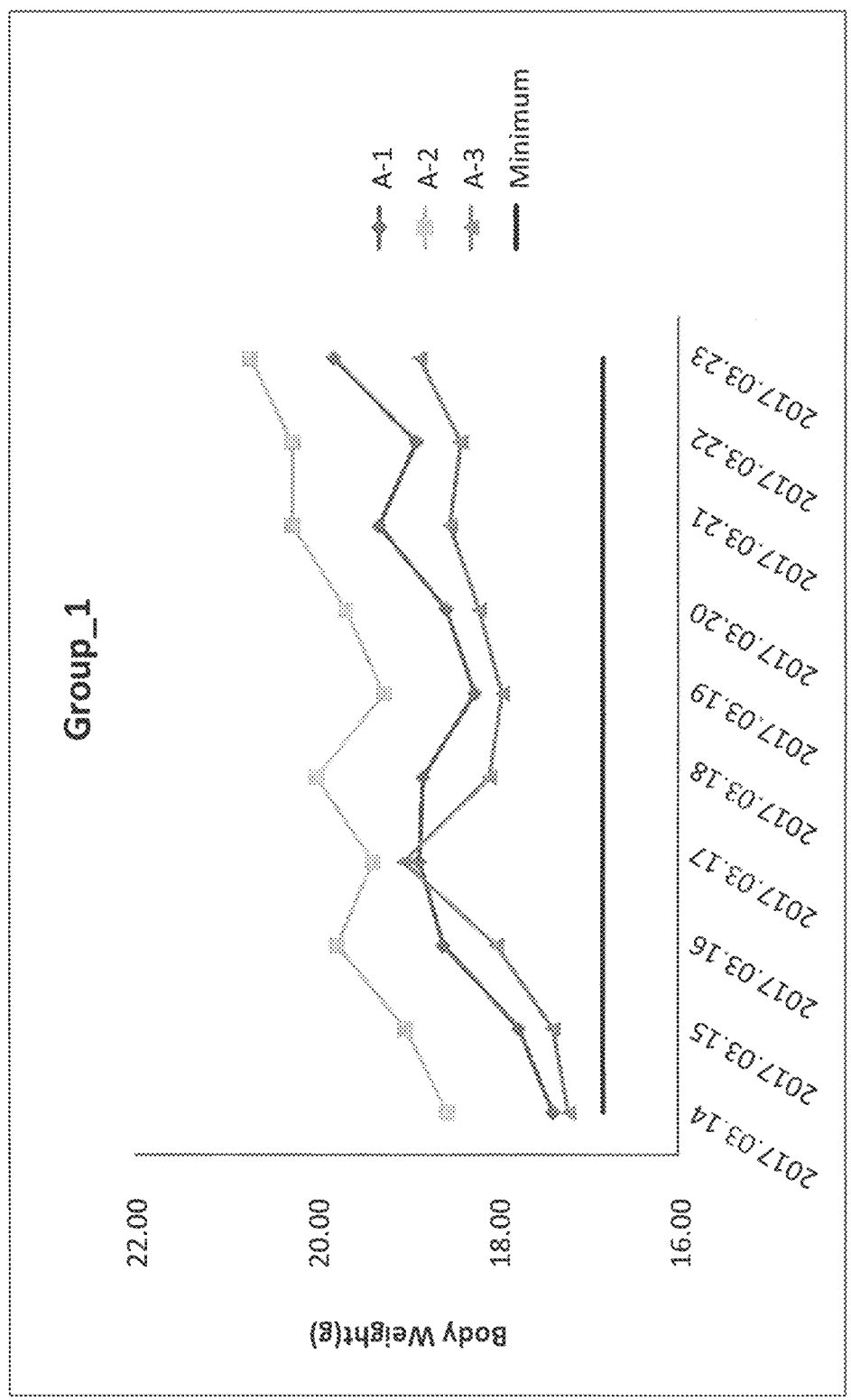
FIGS. 4A-C show that oncolytic viruses had no toxicity to the host.
Figure 4B:
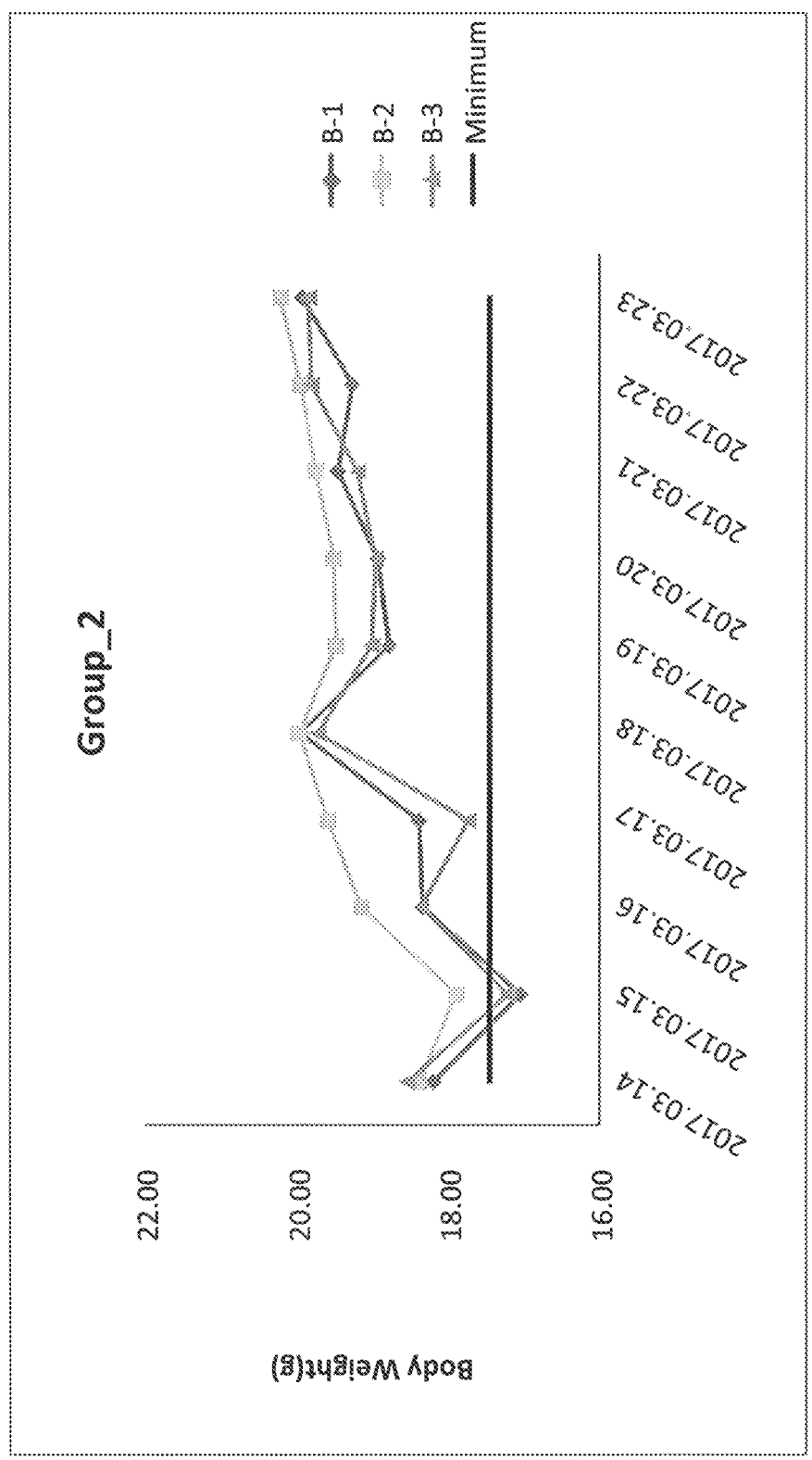
Figure 4C:
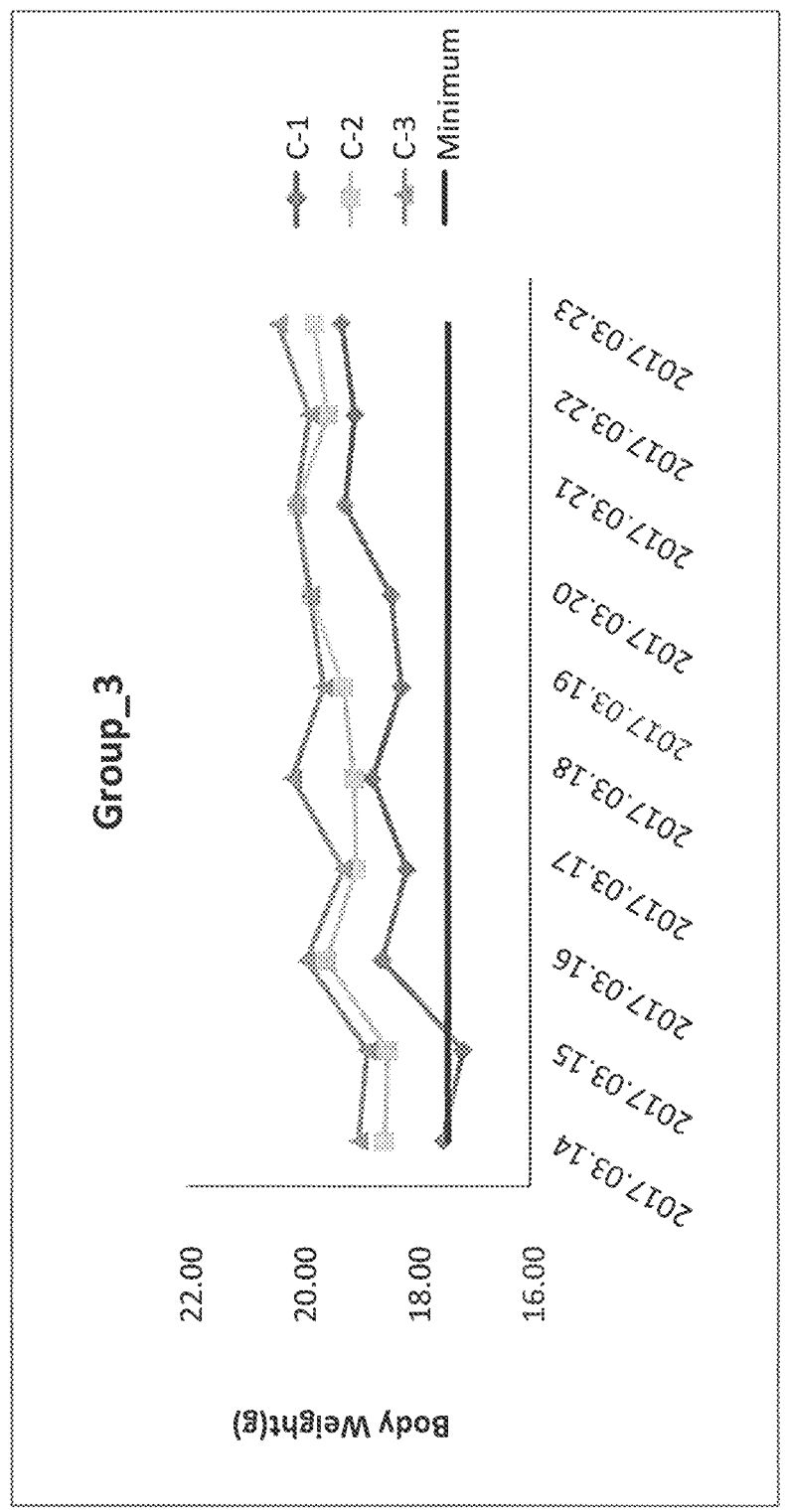

Results
No mice died after virus injection during the test. An electronic balance (supplied from Mettler, Model: ML1602T) was used to measure the body weight one day before the OV was injected, followed daily. No significant differences in mean body weights were observed among the study groups. No groups had an unintentional decline in body weight more than 5%, therefore, the result of the toxicity tests showed that the viruses had no toxicity to the host (FIGS. 4A-C).

Example 5—Evaluation of the Anti-Tumor Activity of OV/GM Combination Therapy in a Murine Melanoma Tumor Model A. Experimental Design
The experimental design is summarized in Table 2:

TABLE 2

| Group | Animals # | Control or GM administration | Control or OV Injection |
|---|---|---|---|
| Control | 15 | PBS: one day before B16-F10 injection, followed by weekly administration, amounting to 4 times | PBS: the first injection was performed based on the tumor volume followed at a 72 hour interval, amounting to 4 times |
| PGM-001 only | 15 | PGM-001: one day before B16-F10 injection, followed by weekly administration, amounting to 4 times | PBS: the first injection was performed based on the tumor volume followed at a 72 hour interval, amounting to 4 times |
| POV-601 only | 15 | PBS: one day before B16-F10 injection, followed by weekly administration, amounting to 4 times | POV-601: the first injection was performed based on the tumor volume followed at a 72 hour interval, amounting to 4 times |

TABLE 2-continued

| Group | Animals # | Control or GM administration | Control or OV Injection |
|---|---|---|---|
| POV-801 only | 15 | PBS: one day before B16-F10 injection, followed by weekly administration, amounting to 4 times | POV-801: the first injection was performed based on the tumor volume followed at a 72 hour interval, amounting to 4 times |
| POV-601 + PGM-001 | 15 | PGM-001: one day before B16-F10 injection, followed by weekly administration, amounting to 4 times | POV-601: the first injection was performed based on the tumor volume followed at a 72 hour interval, amounting to 4 times |
| POV-801 + PGM-001 | 15 | PGM-001: one day before B16-F10 injection, followed by weekly administration, amounting to 4 times | POV-801: the first injection was performed based on the tumor volume followed at a 72 hour interval, amounting to 4 times |

B. Procedure
Test and Control Articles
Test—
Oncolytic Virus (OV): POV-601: $1\times10^8$ PFU/mL; POV-801: $1\times10^8$ PFU/mL
Gut Microbio (GM): PGM-001: $1\times10^9$ CFU/mL
Control—Phosphate Buffered Saline
POV-601 is from CCTCC Deposit No. V201713. POV-801 was obtained from China Center for Type Culture Collection (Wuhan, China, Cat #GDV117). PGM-001 was obtained from Seeking Health (Bellingham, Wash., USA, SKU: PBIFIDO-60-CAPS).
C. Animal Model and Assays
Animals
C57BL/6 female mice, aged between 49~62 days, were supplied from Beijing Vital River Laboratory Animal Technology Co., Ltd. and housed in a standardized animal facility following the Animal Care and Veterinary Services standard operating procedures.
Anti-Tumor Activity Tests in a Murine Subcutaneous Melanoma Tumor Model
GM was formulated at a density according to the Test and Control Articles, and 200 µl of GM was orally administrated into each testing animal one day before the B16-F10 cell injection, followed by the schedule listed in Table 2. To establish a subcutaneous melanoma model, murine B16-F10 melanoma cells harvested from an adherent culture were formulated in PBS at a density of $2\times10^6$/cells, 100 µl of the formulated cells were injected subcutaneously into the right flank of each testing mouse on day 0; and subcutaneous tumors were allowed to grow. Once the group mean tumor volumes reached approximately 20-40 mm³ (about 8~10 days post-injection), each tumor site was injected with 20 µl of either the control (PBS) or the testing OV (POV-601 or POV-801) at a density according to the Test and Control Articles, followed by additional injections at certain time points scheduled in Table 2. All the testing animals were euthanized at day 24 after B16-F10 injection. Those animals whose tumor volume was over 3500 mm³ were sacrificed before the euthanasia day.
Evaluations
Animals dead before their scheduled sacrifice day were discarded without evaluation. Clinical observations were performed everyday to assess mortality. Behavioral observations were performed everyday. Body weight measurement was performed 24 hours following each OV injection. The tumor volume was measured daily using a caliper, and calculated by the formula Tumor volume=L×W²/2.
Data Analysis
All the collected data (tumor size, body weight, and spleen weight) were analyzed with Excel. The anti-tumor effects were compared among all the different testing groups.

Figure 5:
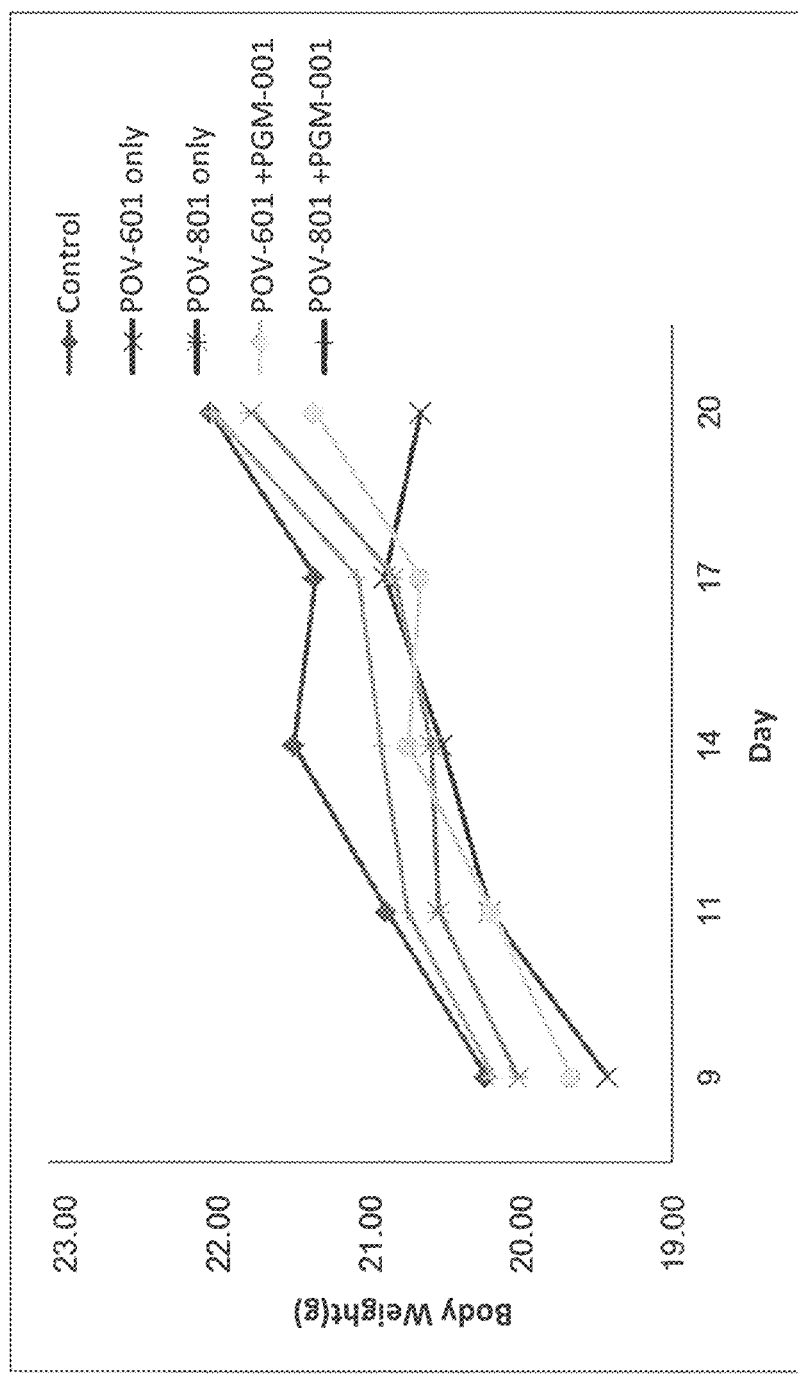
FIG. 5 shows no significant differences in mean body weights among study groups in the evaluation of the anti-tumor activity of OV/GM combination in a murine melanoma tumor model.

D. Results
Clinical Everyday Observations
For the control group, 6 animals were dead on day 15/16/21/22/23; for the POV-801 only group, two animals were found dead on the day 20/22; for the POV-801+PGM-001 group, one animal was found dead on the day 21. No macroscopic lesions were observed for any of the animals.
Body Weight
Body weight was measured once before OV-injection and four times after each OV-injection, amounting to five times during the experiments. There were no significant differences in mean body weights among study groups (FIG. 5).
POV-801+PGM-001 Anti-Tumor Effect and Analysis
FIG. 6 shows the anti-tumor activity of OV/GM combination in a syngeneic murine melanoma tumor model (Total Mice #: Control: 9; POV-801 only: 13; POV-801+PGM-001:14, Mean±SE). PGM-001 as a pre-condition was orally administrated into the groups PGM-001 only and POV-801+PGM-001 the day before the B16-F10 cells injection, B16-F10 injected into each testing animal on the day 0. Tumor-bearing animals were then treated four times subcutaneously (s.c.) with phosphate-buffered saline (PBS) as a control, or treated four times s.c. with POV-801 only, or treated four times s.c. with POV-801 and four times PGM-001 (orally administrated). Tumor volumes were measured on day 10, using a caliper (supplied from Stanley, model: 36-111), followed daily. OV was injected on Day 11, followed at a 72 hour interval (at day 11, 14, 17, 20 after B16-F10 cells injection). Animals were euthanized at day 24 after B16-F10 injection. During the test, a dead animal before its scheduled sacrifice day was discarded without evaluation (FIG. 6). The tumor volume from different groups were compared and calculated by the formula tumor volume=L×W²/2. Bars represent the mean for each group.
POV-601+PGM-001 Anti-Tumor Effect and Analysis
FIG. 7 shows the anti-tumor activity of OV/GM combination in a syngeneic murine melanoma tumor model (Total Mice #: Control: 9; POV-601 only: 13; POV-601+PGM-001:13, Mean±SE). PGM-001 as a pre-condition was orally administrated into the groups PGM-001 only and POV-601+PGM-001 the day before the B16-F10 cells injection, B16-F10-F10 injected into each testing animal on the day 0. Tumor-bearing animals were then treated four times s.c. with phosphate-buffered saline (PBS) as a control, or treated four times s.c. with POV-601 only, or treated four times s.c with POV-601 and four times PGM-001. The tumor volumes were measured on day 10, using a caliper (supplied from Stanley, model: 36-111), followed daily. OV was injected on day 11, followed at a 72 hour interval (at day 11, 14, 17, 20 after cells injection). During the test, a dead animal before its scheduled sacrifice day was discarded without evaluation (FIG. 7). Animals were euthanized at day 24 after B16-F10 injection. The tumor volumes from different groups were compared and calculated by the formula tumor volume=L× $W^2$/2. Bars represent the mean for each group.

Anti-Tumor Effect

The tumor volume ratios from different groups were compared and calculated by the formula=[mean value(Control Group)−mean value (Test Group)]/mean value (Control Group)×100%. The tumor volume data was collected on day 24. The anti-tumor effects are shown in FIG. 8 and Table 3 below.

TABLE 3

Anti-Tumor Effect = [Mean Value (Control Group) − Mean Value (Test Group)]/Mean Value (Control Group) * 100%

| Group | Tumor Volume | Ratio |
|---|---|---|
| Control | 1012.07 | / |
| POV-601 only | 1060.93 | −4.83 |
| POV-801 only | 522.40 | 48.38 |
| POV-601 + PGM-001 | 269.86 | 73.34 |
| POV-801 + PGM-001 | 197.38 | 80.50 |

Example 6—Evaluation of the Anti-Tumor Activity of OV/GM Combination Therapy in a Murine Lung Tumor Model A. Experimental Design The experimental design is summarized in Table 4:

TABLE 4

| Group | Animals # | Control or GM administration | Control or OV Injection |
|---|---|---|---|
| Control | 6 | PBS: two times for a week before B16 injection, followed by weekly administration, amounting to 5 times | PBS: the first injection was 24 hour after B16 injection, followed at a 48 hour interval, amounting to 4 times |
| PGM-001 only | 5 | PGM-001: two times for a week before B16 injection, followed by weekly administration, amounting to 5 times | PBS: the first injection was 24 hour after B16 injection, followed at a 48 hour interval, amounting to 4 times |
| POV-601 only | 5 | PBS: two times for a week before B16 injection, followed by weekly administration, amounting to 5 times | POV-601: the first injection was 24 hour after B16 injection, followed at a 48 hour interval, amounting to 4 times |
| POV-601 + PGM-001 | 5 | PGME-001: two times for a week before B16 injection, followed by weekly administration, amounting to 5 times | POV-601: the first injection was 24 hour after B16 injection, followed at a 48 hour interval, amounting to 4 times |

B. Procedure

Test and Control Articles

Test—

Oncolytic Virus (OV): POV-601:1×$10^8$ PFU/mL

Gut Microbio (GM): PGM-001:1×$10^9$ CFU/mL

Control—Phosphate Buffered Saline

POV-601 is from CCTCC Deposit No. V201713. POV-801 was obtained from China Center for Type Culture Collection (Wuhan, China, Cat #GDV117). PGM-001 was obtained from Seeking Health (Bellingham, Wash., USA, SKU: PBIFIDO-60-CAPS).

C. Animal Model and Assays

Animals

C57BL6 female mice, aged between 49~62 days, were supplied from Beijing Vital River Laboratory Animal Technology Co., Ltd. and housed in a standardized animal facility following the Animal Care and Veterinary Services standard operating procedures.

Anti-Tumor Activity Tests in a Murine Lung Tumor Model

GM was formulated at a density, and 200 ul of GM was orally administrated into each testing animal two times for a week before the B16-F10 cell injection, followed by the schedule listed in Table 4. To establish a lung tumor model, murine B16-F10 melanoma cells harvested from an adherent culture were formulated in PBS at a density of 3×$10^6$/cells, and 100 µl of the formulated cells were injected intravenously into each testing mouse on day 0. Lungs were excised and surface metastases were counted on day 10 or 14. On Day 1, each testing animal was injected with 100 µl of control (PBS) or the testing OV (POV-601) at the titers shown in the Test and Control Articles section, followed by additional injections at certain time points scheduled in Table 4. On Day 10, one mice from the control group were euthanized, and its lung was harvested and examined for tumor formation. In the case that there were few tumors formed on the lung surface, all the testing animals would be euthanized on Day 14.

Evaluations

Animals dead before their scheduled sacrifice day were discarded without evaluation. Clinical observations were performed everyday to assess mortality. Behavioral observations were performed everyday. Body weight measurement was performed twice (days −9 and 0) before the first OV injection and five times on days 2, 5, 7, 11, 15. The spleen from each testing animal was harvested at the euthanasia day and weighed with an electronic balance (supplied from Mettler, Model: ML1602T). To assess lung metastasis, the lung from each testing animal was harvested at the euthanasia day and the lung metastases (black tumor spots) were counted.

Data Analysis

All the collected data (lung metastases, body weight, and spleen weight) were analyzed with Excel. The anti-tumor effects were compared among all the different testing groups.

D. Results

Clinical Everyday Observations

For the control group, one animal was euthanized on the day 10 to evaluate tumor formation. No enough tumor spots were observed, and therefore all the testing animals were allowed to continually be housed until euthanized at day 14.

Body Weight

Figure 9:
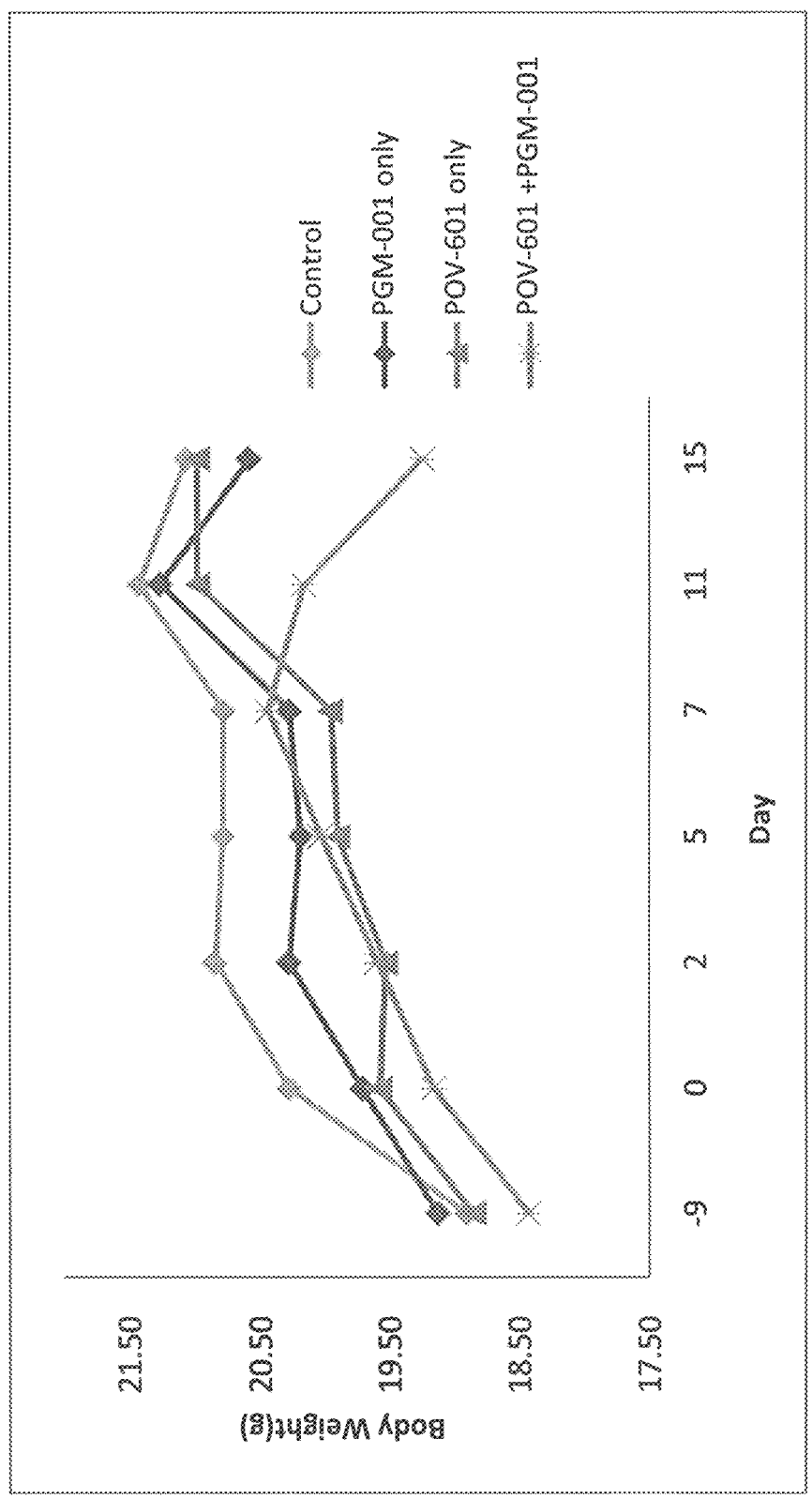
FIG. 9 shows no significant differences in mean body weights among study groups in the evaluation of the anti-tumor activity of OV/GM combination in a murine lung tumor model.

Body weight was measured twice (days −9 and 0) before OV-injection and five times on days 2, 5, 7, 11, 15, amount to seven times during the experiment. There was no significant changes in mean body weights among all the study groups. (FIG. 9).

Weight of Spleen

Figure 10:
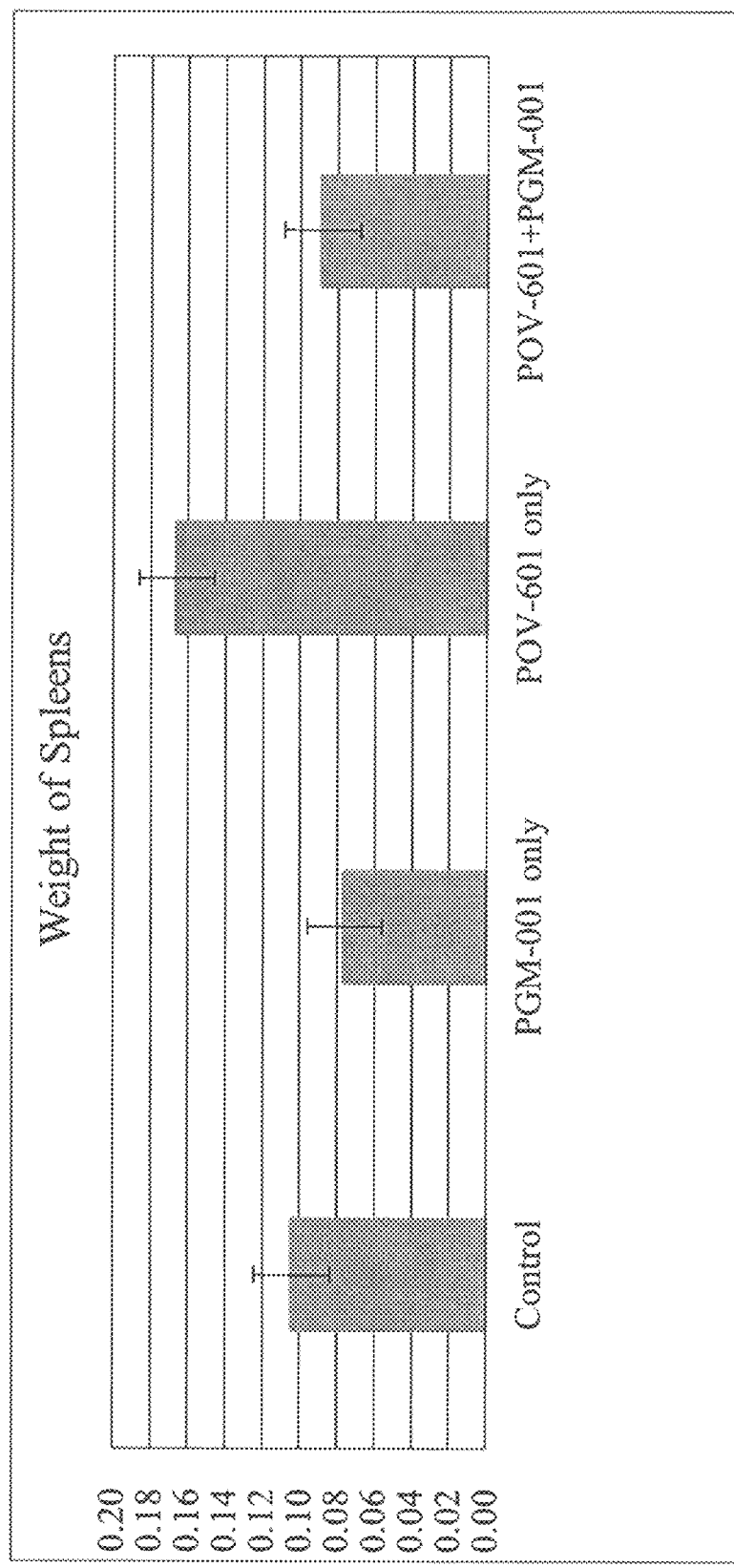
FIG. 10 shows no significant differences in mean spleen weights among study groups in the evaluation of the anti-tumor activity of OV/GM combination in a murine lung tumor model.

Mice from all groups were euthanized at day 14 after the B16-F10 injection. Through dissection, the spleens of all mice were removed and measured respectively (in grams). No significant differences in mean spleen weights among study groups were observed (FIG. 10).

POV-601+PGM-001 Anti-Tumor Effect

Mice from all groups were euthanized at day 14 after the B16-F10 injection, and lungs were harvested and put into cold PBS to count lung metastasis. The amount of black tumor spots on the lung surface for each mouse was counted with the naked eye. During the test, an animal in the control group was sacrificed at day 10, and the data from this animal was not included in the analyzed data in FIG. 11. FIG. 11 shows the results of the control, PGM-001 only, POV-601 only, and POV-601+PGM-001 treatment groups.

The invention claimed is:

1. A method of treating cancer comprising:
orally administering to a subject an effective amount of about $10^9$ to $10^{11}$ cfu of gut microbiota of the genus *Bifidobacterium*; and
from about one week to two months after the gut microbiota are administered, intravenously or intratumorally administering to the subject an effective amount of about $10^5$ to $10^{10}$ pfu of an oncolytic ORF virus having anticancer activity and that selectively targets tumor cells;
wherein the gut microbiota pre-conditions the subject's immune system to antitumor responses and augments the anticancer activity of the oncolytic ORF virus, and
wherein a platform is created to identify potential elite responders to the oncolytic ORF virus treatment based on an abundance of the subject's particular gut microbiota.

2. The method according to claim 1, wherein the platform is built through hierarchical clustering analysis of genomic profiles of the human gut microbiome and identifies the gut microbiota that suppress tumor progression.

3. The method according to claim 2, wherein the identified elite responders are predicted to respond favourably to the oncolytic ORF virus based on the abundance of the subject's particular gut microbiota.

4. The method according to claim 1, wherein the cancer is melanoma.

5. The method according to claim 1, wherein the cancer is lung cancer.

6. The method according to claim 1, wherein the cancer is kidney cancer.

7. The method according to claim 1, wherein the cancer is glioma.

8. The method according to claim 1, wherein the cancer is triple negative breast cancer.

9. The method according to claim 1, wherein the cancer is renal cancer.

* * * * *

UNITED STATES PATENT AND TRADEMARK OFFICE
CERTIFICATE OF CORRECTION

| | |
|---|---|
| PATENT NO. | : 11,433,108 B2 |
| APPLICATION NO. | : 15/744295 |
| DATED | : September 6, 2022 |
| INVENTOR(S) | : Minjie Hu et al. |

It is certified that error appears in the above-identified patent and that said Letters Patent is hereby corrected as shown below:

On the Title Page

Item (57), Line 5 of ABSTRACT, "oncolytic vims" should read --oncolytic virus--.

Signed and Sealed this
Eighteenth Day of April, 2023

Katherine Kelly Vidal
*Director of the United States Patent and Trademark Office*